United States Patent
Miyamoto et al.

(10) Patent No.: US 10,027,183 B2
(45) Date of Patent: Jul. 17, 2018

(54) DETECTING APPARATUS, POWER RECEIVING APPARATUS, POWER TRANSMITTING APPARATUS, AND CONTACTLESS POWER SUPPLY SYSTEM

(71) Applicant: SONY CORPORATION, Tokyo (JP)

(72) Inventors: Takashi Miyamoto, Chiba (JP); Kohei Mori, Tokyo (JP); Tomomichi Murakami, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/153,530

(22) Filed: May 12, 2016

(65) Prior Publication Data

US 2016/0336814 A1 Nov. 17, 2016

Related U.S. Application Data

(63) Continuation of application No. 13/790,981, filed on Mar. 8, 2013, now Pat. No. 9,360,442.

(30) Foreign Application Priority Data

Mar. 14, 2012 (JP) .................................. 2012-057537

(51) Int. Cl.
*G01V 3/10* (2006.01)
*H02J 50/12* (2016.01)
(Continued)

(52) U.S. Cl.
CPC .............. *H02J 50/60* (2016.02); *G01N 27/00* (2013.01); *G01N 27/72* (2013.01); *G01V 3/101* (2013.01);
(Continued)

(58) Field of Classification Search
CPC ........ G01N 27/00; G01N 27/72; G01V 3/101; H02J 50/12; H02J 50/60; H02J 7/025; H04B 5/0037; H04B 5/0087
(Continued)

(56) References Cited

U.S. PATENT DOCUMENTS 4,816,765 A * 3/1989 Boskamp ............. G01R 33/341 324/318
6,480,614 B1 * 11/2002 Denda ...................... H04R 7/04 381/191

(Continued)

FOREIGN PATENT DOCUMENTS

| JP | 2009-076513 A | 4/2009 |
| JP | 2010-164472 A | 7/2010 |

(Continued)

OTHER PUBLICATIONS

Office Action for CN Patent Application No. 201310070594.9, dated Jul. 12, 2016, 11 pages of Office Action and 7 pages of English Translation.

(Continued)

*Primary Examiner* — Thienvu Tran
*Assistant Examiner* — Brian K Baxter
(74) *Attorney, Agent, or Firm* — CHIP LAW GROUP

(57) ABSTRACT

There is provided a detecting apparatus including one or a plurality of magnetic coupling elements that include a plurality of coils, and a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present. In the one or plurality of magnetic coupling elements, the plurality of coils are electrically connected such that mag- (Continued)

netic flux produced from at least one or more of the plurality of coils and magnetic flux produced from remaining coils of the plurality of coils have approximately opposing orientations.

16 Claims, 17 Drawing Sheets

(51) Int. Cl.
    *H02J 50/60* (2016.01)
    *G01N 27/00* (2006.01)
    *G01N 27/72* (2006.01)
    *H02J 7/02* (2016.01)
    *H04B 5/00* (2006.01)

(52) U.S. Cl.
    CPC .............. *H02J 7/025* (2013.01); *H02J 50/12* (2016.02); *H04B 5/0037* (2013.01); *H04B 5/0087* (2013.01)

(58) Field of Classification Search
    USPC ........................................................ 307/104
    See application file for complete search history.

(56) References Cited

U.S. PATENT DOCUMENTS

| | | |
|---|---|---|
| 8,957,549 B2 | 2/2015 | Kesler et al. |
| 9,106,203 B2 | 8/2015 | Kesler et al. |
| 2006/0049928 A1 | 3/2006 | Ening et al. |
| 2007/0120636 A1 | 5/2007 | Chen et al. |
| 2007/0145830 A1 | 6/2007 | Lee et al. |
| 2008/0024255 A1 | 1/2008 | Sano |
| 2008/0252151 A1* | 10/2008 | Binnard ............... G03F 7/70758 310/12.06 |
| 2009/0079387 A1* | 3/2009 | Jin ........................ H02J 7/0004 320/108 |
| 2010/0328045 A1* | 12/2010 | Goto ..................... G06K 7/0008 340/10.4 |
| 2011/0101788 A1* | 5/2011 | Sun ........................ H01F 38/14 307/104 |
| 2011/0309994 A1* | 12/2011 | Kato .................... H01P 1/20345 343/860 |
| 2012/0049991 A1* | 3/2012 | Baarman ............. H01F 17/0013 336/199 |
| 2012/0146580 A1* | 6/2012 | Kitamura ............... H01F 38/14 320/108 |
| 2012/0256494 A1 | 10/2012 | Kesler |
| 2013/0024059 A1* | 1/2013 | Miller ..................... H01F 38/14 701/22 |
| 2013/0069441 A1 | 3/2013 | Verghese et al. |
| 2013/0093257 A1 | 4/2013 | Goto |
| 2013/0119927 A1* | 5/2013 | Partovi .................. H02J 7/025 320/108 |
| 2013/0207763 A1 | 8/2013 | Wagoner et al. |

FOREIGN PATENT DOCUMENTS

| | | |
|---|---|---|
| JP | 2011-072074 A | 4/2011 |
| JP | 2013-046526 A | 3/2013 |
| WO | 2010/118191 A1 | 10/2010 |
| WO | 2013/036947 A2 | 3/2013 |

OTHER PUBLICATIONS

Office Action for JP Patent Application No. 2016-133024, dated May 9, 2017, 08 pages of Office Action and 08 pages of English Translation.

\* cited by examiner

FIRST COMPARATIVE
EXAMPLE
(INSIDE DIAMETER
OF L2 >
INSIDE DIAMETER
OF L4)

SECOND
COMPARATIVE
EXAMPLE
(INSIDE DIAMETER
OF L2 =
INSIDE DIAMETER
OF L4)

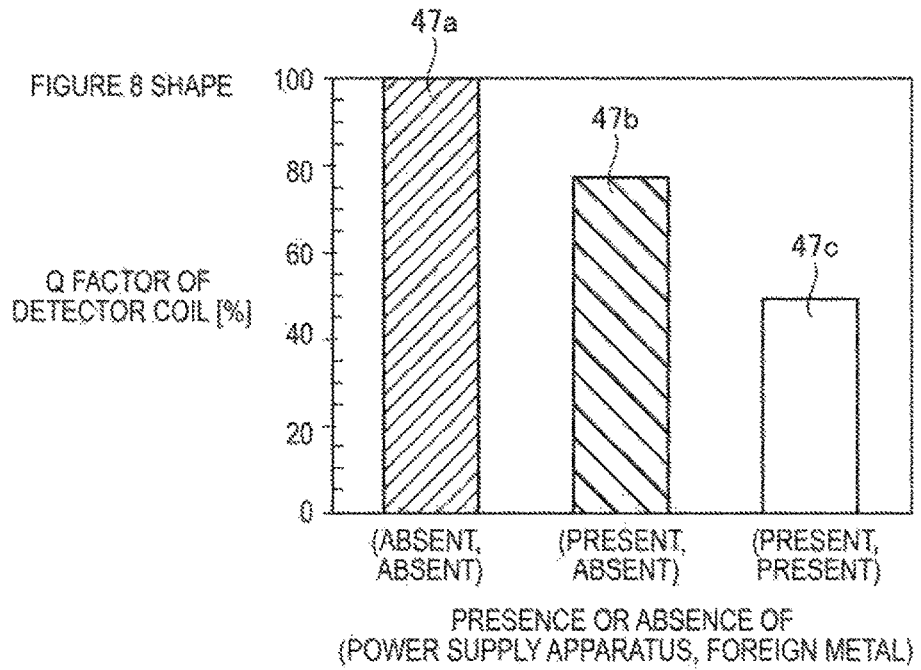
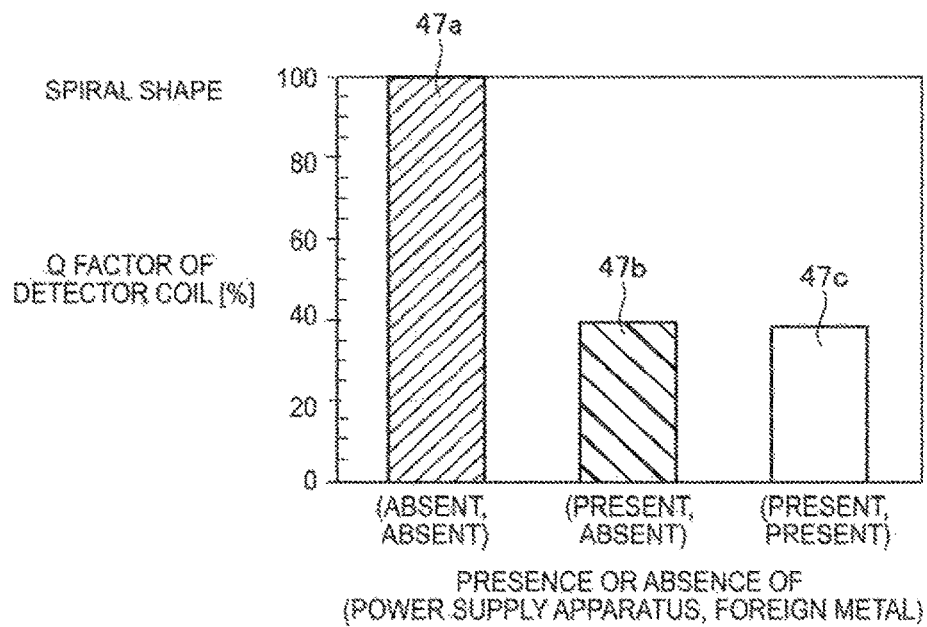

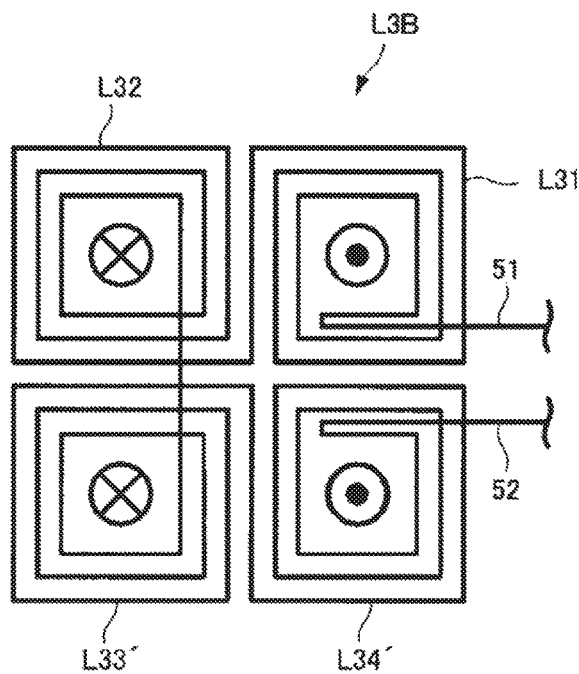
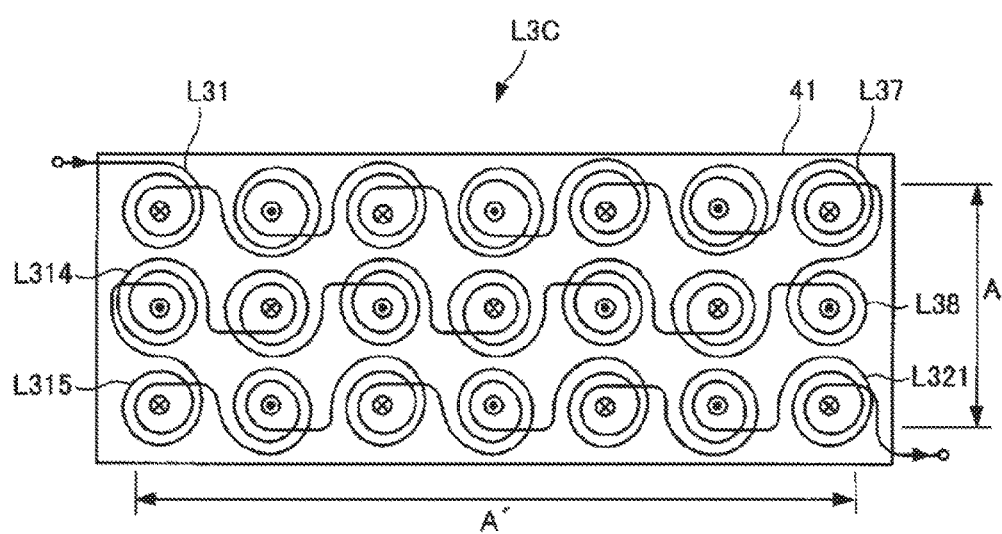

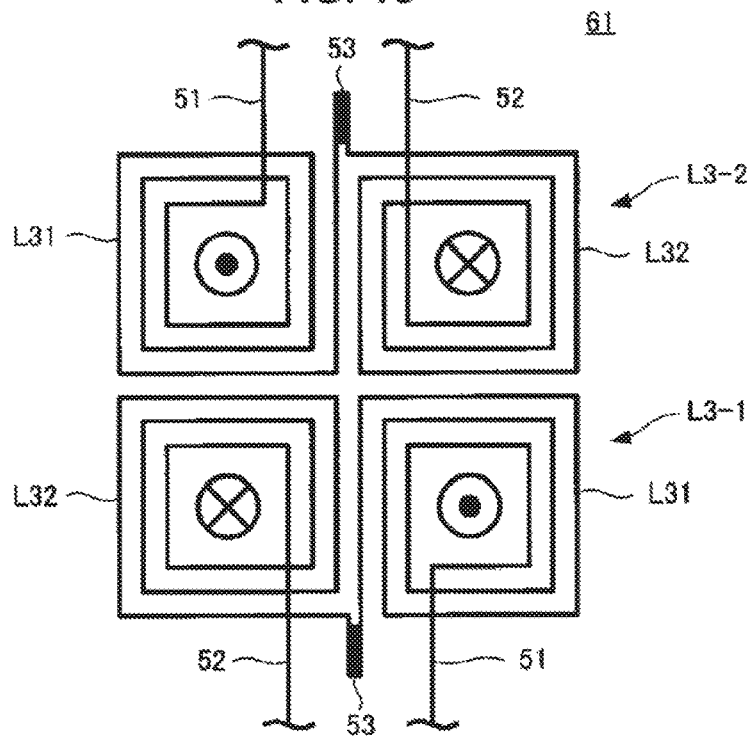
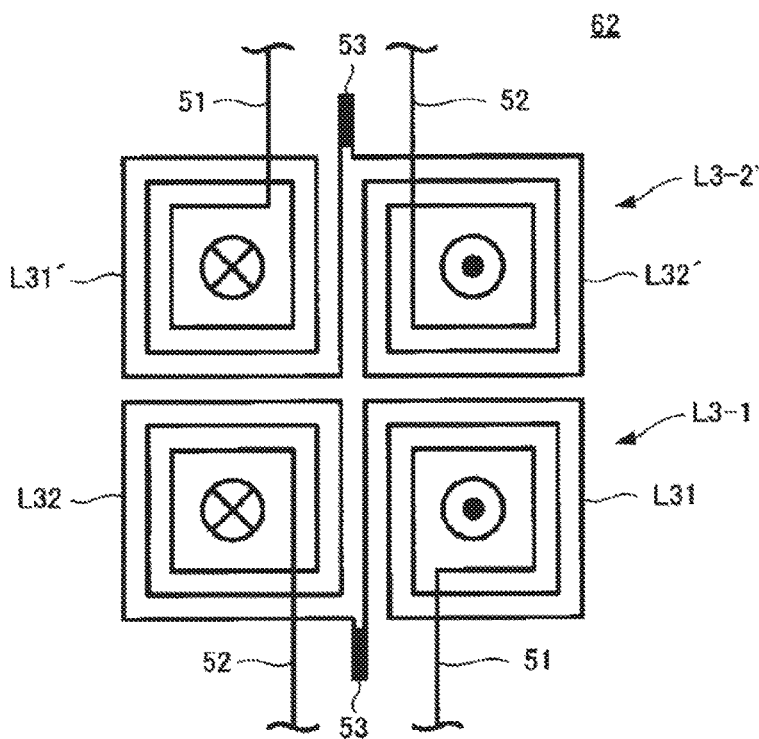

DETECTING APPARATUS, POWER RECEIVING APPARATUS, POWER TRANSMITTING APPARATUS, AND CONTACTLESS POWER SUPPLY SYSTEM

CROSS-REFERENCE TO RELATED APPLICATIONS

The present application is a continuation application of U.S. patent application Ser. No. 13/790,981, filed Mar. 8, 2013, which claims the benefit of priority from prior Japanese Priority Patent Application JP 2012-057537 filed in the Japan Patent Office on Mar. 14, 2012, the entire content of which is hereby incorporated by reference.

BACKGROUND

The present disclosure relates to a magnetic coupling element that magnetically couples with another magnetic coupling element or foreign matter, and to an apparatus (magnetic coupling apparatus) and system (magnetic coupling system) utilizing such a magnetic coupling element.

More particularly, the present disclosure relates to a detecting apparatus, a power receiving apparatus, a power transmitting apparatus, and a contactless power supply system configured to detect the presence of foreign matter (such as metal, a magnetized body, or magnet) which may generate heat due to magnetic flux between a contactless power supplying apparatus and an electronic device constituting a contactless power supply system.

Recently, increasing attention is being given to power supply systems that supply power (transfer power) to a consumer electronics (CE) device, such as a mobile phone or portable music player, for example, in a contactless manner (referred to as contactless power supply systems or contactless power transfer systems, for example). With such systems, charging is initiated not by inserting (connecting) the connector of an AC adapter or other power supply apparatus into a CE device, but rather by simply placing an electronic device (the secondary device) onto a charging tray (the primary device). In other words, a terminal connection between the electronic device and the charging tray is unnecessary.

Electromagnetic induction is established as a technique for supplying power in a contactless manner as above. Meanwhile, contactless power supply systems using a technique called magnetic resonance which utilizes the resonance phenomenon have been gaining attention recently.

Contactless power supply systems using magnetic resonance are advantageous in that the principle of the resonance phenomenon may be utilized to transfer power between devices separated by greater distances than those of electromagnetic induction. Additionally, there is an advantage in that the transfer efficiency (power supply efficiency) does not fall significantly even if the axis alignment between the power source (transmitter coil) and power recipient (receiver coil) is somewhat poor. However, magnetic resonance-based systems and electromagnetic induction-based systems are alike in that both are contactless power supply systems (magnetic coupling systems) utilizing a power source (transmitter coil; a magnetic coupling element) and a power recipient (receiver coil; a magnetic coupling element).

Meanwhile, one important element in contactless power supply systems is the thermal regulation of foreign matter, such as metals, magnetized bodies, and magnets, which may generate heat due to magnetic flux. If foreign matter becomes interposed in the gap between the transmitter coil and the receiver coil when supplying power in a contactless manner, there is a risk of causing the foreign matter to generate heat due to the magnetic flux passing through that foreign matter. This risk is not limited to electromagnetic induction-based or magnetic resonance-based systems. Such heat generation in foreign matter may lead to currents being produced in a foreign metal due to the magnetic flux passing through the foreign metal (eddy currents, current loops, circular currents), or to hysteresis loss being produced in a foreign magnetized body or foreign magnet due to the magnetic flux passing through the foreign magnetized body or foreign magnet.

A large number of techniques that detect foreign metal by adding a foreign matter detection system to a contactless power supply system have been proposed for such thermal regulation. For example, techniques using an optical sensor or a temperature sensor have been proposed. However, detection methods that use sensors may be costly in the case of a broad power supply range, as with magnetic resonance-based systems. Moreover, use of a temperature sensor, for example, may impose additional design constraints on the transmitting and receiving devices, since the output results from the temperature sensor will depend on its surrounding thermal conductivity.

Thus, there have been proposed techniques that determine the presence of foreign metal by looking at changes in parameters (such as current and voltage) when a foreign metal comes between the transmitter and receiver. With such techniques, it is possible to curtail costs without imposing design or other constraints.

For example, JP 2008-206231A proposes a method of detecting foreign metal according to the modulation rate (information on amplitude and phase changes) during communication between the transmitter and receiver, while JP 2001-275280A proposes a method of detecting foreign metal according to eddy current loss (foreign matter detection according to DC-DC efficiency).

SUMMARY

However, the techniques proposed in JP 2008-206231A and JP 2001-275280A do not take into account the effects of a metal housing at the receiver. Consider the case of charging a typical portable device. It is highly probably that some kind of metal (such as a metal housing or metal components) is used in the portable device, and thus it is difficult to clearly determine whether a change of parameters is due to the effects of the metal housing or components, or due to the presence of foreign metal. To take JP 2001-275280A as an example, it is indeterminate whether eddy current loss occurs because of the metal housing of the portable device, or because foreign metal is present between the transmitter and receiver. In this way, it can hardly be said that the techniques proposed in JP 2008-206231A and JP 2001-275280A are able to accurately detect foreign metal.

Being devised in light of the above circumstances, an embodiment according to the embodiment of the present disclosure detects foreign matter in close proximity to a detector coil (in other words, a magnetic coupling element) without providing an additional sensor, and furthermore improves detection accuracy.

According to an embodiment of the present disclosure, there is provided a detecting apparatus including one or a plurality of magnetic coupling elements that include a plurality of coils, and a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present. In the one or plurality of magnetic coupling elements, the plurality of coils are electrically connected such that magnetic flux produced from at least one or more of the plurality of coils and magnetic flux produced from remaining coils of the plurality of coils have approximately opposing orientations.

According to an aspect of the present disclosure, it is possible to realize significant improvement regarding issues such as magnetic flux leakage from a magnetic coupling element, change in the electrical properties (electrical parameters) of a magnetic coupling element due to external factors, and unwanted noise occurring in a magnetic coupling element.

According to at least one aspect of the present disclosure, it is possible, without providing an additional sensor, to detect foreign matter which is in close proximity to a magnetic coupling element and which may generate heat due to magnetic flux, and furthermore greatly improve detection accuracy.

BRIEF DESCRIPTION OF THE DRAWINGS

FIG. 6A is an exemplary perspective view configuration and FIG. 6B is an exemplary plan view configuration of the detector coil and receiver coil in the case where the difference between the inner dimension of the detector coil and the inner dimension of the receiver coil is −4 mm;

FIG. 7A illustrates an exemplary plan view configuration of the detector coil and receiver coil in the case where the difference between the inner dimension of the detector coil and the inner dimension of the receiver coil is 0 mm, and FIG. 7B is an exemplary plan view configuration of the detector coil and receiver coil in the case where the difference between the inner dimension of the detector coil and the inner dimension of the receiver coil is +4 mm;

FIG. 8A illustrates an exemplary detailed configuration of the detector coil and receiver coil in the case where the difference between the inner dimension of the detector coil and the inner dimension of the receiver coil is −4 mm, and FIG. 8B is an exemplary detailed configuration of the detector coil and receiver coil in the case where the difference between the inner dimension of the detector coil and the inner dimension of the receiver coil is 0 mm;

FIG. 10A is a diagrammatic cross-section view regarding a spiral-shaped coil and the distribution of magnetic field lines produced from that coil, while

FIG. 11A is a waveform diagram illustrating an example of a waveform of voltage (voltage waveform) produced in an LC resonator (resonant circuit) including a detector coil and a resonant capacitor C3 in the case where a spiral-shaped detector coil is disposed inside the receiver coil illustrated in FIG. 8A, while

FIG. 13A is a performance mapping illustrating exemplary foreign metal detection accuracy for the case of using a figure 8-shaped coil as a detector coil, while FIG. 13B is a performance mapping illustrating exemplary foreign metal detection accuracy for the case of using a spiral-shaped coil as a detector coil;

FIG. 16 is a plan view illustrating an exemplary configuration of a square grid-shaped detector coil according to a first modification of the second embodiment of the present disclosure;

FIG. 17 is a plan view illustrating an exemplary configuration of a lattice-shaped detector coil according to the third embodiment of the present disclosure;

FIG. 18 is a plan view illustrating an example of a detector coil unit in which two figure 8-shaped detector coils are disposed according to the fourth embodiment of the present disclosure;

FIG. 19 is a plan view illustrating an example of a detector coil unit in which two figure 8-shaped detector coils are disposed according to a first modification of the fourth embodiment of the present disclosure;

FIGS. 20A, 20B, and 20C are plan views illustrating an example of a receiver coil, an example in which multiple detector coils are disposed on top of the receiver coil, and an example in which some detector coils are disposed in the center of the receiver coil, respectively;

FIGS. 21A, 21B, and 21C are plan views illustrating an example of a receiver coil and foreign metal, an example in which multiple detector coils are disposed on top of the receiver coil, and an example in which multiple detector coils are additionally disposed on top of the multiple detector coils in FIG. 21B, respectively; FIGS. 22A and 22B are plan views illustrating an example in which multiple detector coils are disposed on top of the receiver coil, and an example in which multiple detector coils are additionally disposed on top of the multiple detector coils in FIG. 22A, respectively.

DETAILED DESCRIPTION OF THE EMBODIMENT(S)

Figure 1:
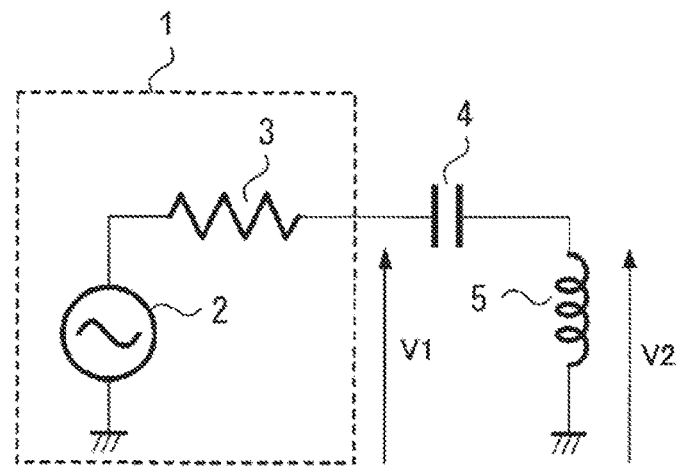
FIG. 1 is a schematic circuit diagram accompanying an explanation of Q factor measurement used as an example of foreign metal detection according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Hereinafter, the description will proceed in the following order.
1. Introductory explanation
2. First embodiment (example of magnetic coupling element with figure 8-shaped detector coil)
3. Second embodiment (example of magnetic coupling element with square grid-shaped detector coil)
4. Third embodiment (example of magnetic coupling element with lattice-shaped detector coil)
5. Fourth embodiment (example of magnetic coupling element using two figure 8-shaped detector coils)
6. Fifth embodiment (example of magnetic coupling element disposing multiple detector coils on top of receiver coil)
7. Sixth embodiment (example of magnetic coupling element disposing multiple detector coils over wide range on top of receiver coil)
8. Other
<1. Introductory Explanation>

In the present disclosure, there is proposed a magnetic coupling system that detects foreign matter on the basis of an electrical parameter for a circuit at a transmitter or a receiver when charging a component such as a battery in the receiver (secondary device) with power supplied from the transmitter (primary device). In a magnetic coupling system according to an embodiment of the present disclosure, an electrical parameter is measured for a circuit in a transmitter or a receiver, the circuit at least including one or multiple magnetic coupling elements which magnetically couple with an external element and which are realized with multiple coils. The presence of foreign matter in close proximity to the magnetic coupling element is then determined on the basis of the electrical parameter measurement results.

Hereinafter, a description will be given using, as an example, the case where the above circuit at least including a magnetic coupling element is a resonant circuit, while in addition, the above electrical parameter is the quality factor (Q factor). The Q factor is an index expressing the relationship between energy storage and loss, and is typically used as a factor expressing the sharpness of the resonance peak (in other words, the resonance strength) in a resonant circuit.

Note that although the descriptions of the respective embodiments of the present disclosure in this specification cite the detection of foreign metal as an example, the detection of other foreign matter (such as foreign magnetized bodies and foreign magnets) is also similar.
[Q Factor Measurement Principle]

Hereinafter, the principle of Q factor measurement will be described with reference to the drawings.

FIG. 1 is a schematic circuit diagram accompanying an explanation of Q factor measurement used for foreign metal detection according to an embodiment of the present disclosure.

The circuit illustrated in FIG. 1 is an example of a basic circuit layout (for the case of magnetic coupling) illustrating the principle of Q factor measurement. The circuit is provided with a signal source 1, which includes an alternating current (AC) power source 2 that produces an AC signal (sine wave) and a resistive element 3, as well as a capacitor 4 and a coil 5. The resistive element 3 is an illustration of the internal resistance (output impedance) of the AC power source 2. The capacitor 4 and the coil 5 are connected to the signal source 1 so as to form a series resonant circuit (one example of a resonant circuit). The resonant circuit resonates at a given frequency (the resonant frequency) according to the capacitance value (C value) of the capacitor 4 and the inductance value (L value) of the coil 5.

Although FIG. 1 illustrates a circuit provided with a series resonant circuit realized with a coil 5 and a capacitor 4, various layouts are conceivable for the detailed configuration, insofar as resonant circuit functionality is provided.

If foreign metal, such as a metal fragment, for example, is present near the coil 5, the magnetic field lines will pass through the metal fragment, and eddy currents will be produced in the metal fragment. From the perspective of the coil 5, the metal fragment and the coil 5 are magnetically coupled and it appears as though a resistive load has been attached to the coil 5, changing the Q factor of the coil (resonant circuit). Measuring the Q factor thus leads to detection of foreign metal near the coil 5 (in other words, a magnetically coupled state).

At this point, take V1 to be the voltage across the ends of the coil 5 and the capacitor 4 constituting the series resonant circuit (an example of voltage applied to a resonant circuit), and take V2 to be the voltage across the ends of the coil 5. In this case, the Q factor of the series resonant circuit is expressed as in Eq. 1, where R is the effective resistance value (series resistance value) for the frequency f of the circuit, L is the inductance value, and C is the capacitance value. When V2>>V1, the equation may be approximated as follows.

$$Q = \frac{1}{R}\sqrt{\frac{L}{C}} = \frac{V2 - V1}{V1} \cong \frac{V2}{V1} \qquad (1)$$

In the circuit illustrated in FIG. 1, the voltage V2 is obtained by multiplying the voltage V1 by a factor of approximately Q. It is established that the series resistance value R and the inductance value L indicated in Eq. 1 change as metal approaches or due to the effects of eddy currents produced in the metal. For example, if a metal fragment approaches the coil 5, the effective resistance value R increases, and the Q factor drops. In other words, since the Q factor of the resonant circuit and the resonant frequency change greatly due to the effects of metal present in the vicinity of the coil 5, by detecting such change it is possible to detect a metal fragment present near the coil 5. Additionally, such Q factor measurement may be applied to the detection of foreign metal interposed between a transmitter (primary device) and a receiver (secondary device).

By conducting a foreign metal detection process using changes in the Q factor discussed above, it is possible to detect foreign metal with high accuracy for both electromagnetic induction-based systems and magnetic resonance-based systems, and have the user remove the detected foreign metal.

[Overview of Technology According to the Embodiment of Present Disclosure]

Meanwhile, another conceivable technique involves using a detector connected to a circuit including a coil (detector coil) that electromagnetically or magnetically couples with an external element to measure the Q factor of the circuit using an AC signal at a different frequency than the frequency of the AC signal flowing through the transmitter coil and the receiver coil.

Also, as another example, a configuration in which the above detector coil used to measure the Q factor is separate from the transmitter coil and the receiver coil is also conceivable.

By using an AC signal at a different frequency than the frequency of the AC signal flowing through the transmitter coil and the receiver coil, AC signals for contactless power supply are separable from AC signals for Q factor measurement, and thus it becomes possible to measure the Q factor while contactless power supply is in operation. In addition, accurate detection of foreign metal or other matter may be conducted even while contactless power supply is in operation.

However, the detector coil may be greatly affected by the magnetic flux (lines of magnetic force; a magnetic field) for contactless power supply in the case of using a typical spiral-shaped coil 5 as the detector coil that electromagnetically or magnetically couples with an external element. As a result, AC signals for Q factor measurement utilized in foreign matter detection may overlap AC signals for contactless power supply, producing unwanted noise due to the contactless power supply. As a result, foreign metal detection accuracy may decrease greatly.

Also, the above detector coil is readily affected by the transmitter coil and receiver coil used for contactless power supply, as well as by elements such as magnetic materials and metal inside the electronic device housing. Given this issue, if a typical spiral-shaped detector coil is packaged in a device such as a contactless power supply apparatus (hereinafter simply designated "power supply apparatus") or electronic device, the Q factor of the detector coil, which is used as the basis value for determining the presence of foreign metal, may decrease greatly.

Furthermore, foreign metal detection accuracy may change greatly depending on the configuration of the power source (transmitter) and power recipient (receiver) in the contactless power supply system.

In this way, it has been difficult to obtain exact information for foreign matter detection, and the foreign matter detection accuracy has not improved. Accordingly, the inventors propose a magnetic coupling element that improves foreign matter detection accuracy by obtaining more exact information for foreign matter detection, as well as a foreign matter detecting apparatus using such a magnetic coupling element.

<1. First Embodiment>
[Exemplary Overall Configuration of Contactless Power Supply System]

Figure 2:
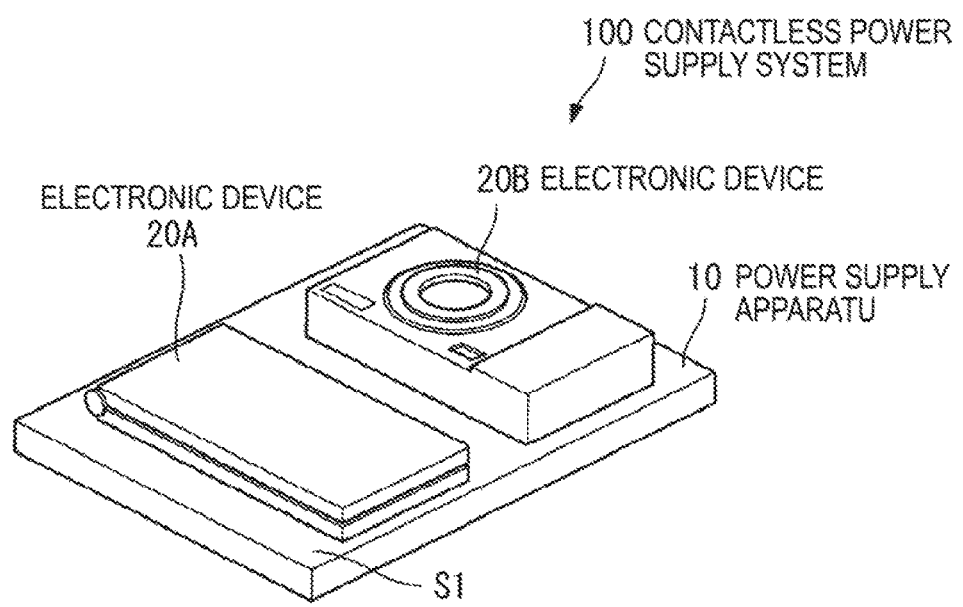
FIG. 2 is a diagrammatic exterior illustration of a contactless power supply system according to the first embodiment of the present disclosure.
Figure 3:
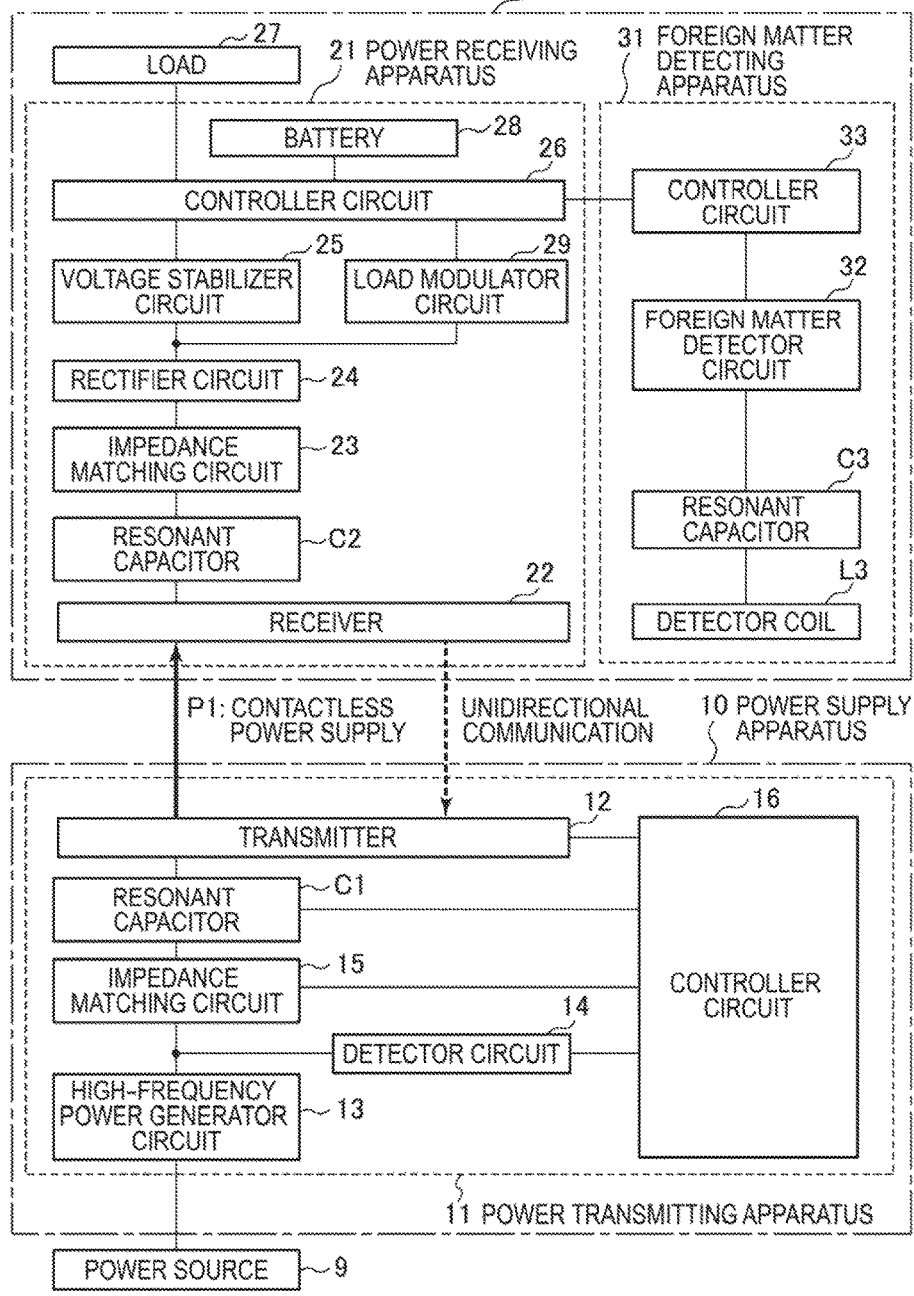
FIG. 3 is a block diagram illustrating an exemplary configuration of a contactless power supply system according to the first embodiment of the present disclosure.

FIG. 2 illustrates an exemplary diagrammatic configuration of a contactless power supply system given as a magnetic coupling system according to the first embodiment of the present disclosure, while FIG. 3 illustrates an exemplary block configuration of a contactless power supply system according to the first embodiment of the present disclosure.

The contactless power supply system 100 illustrated in FIG. 2 is a system that transfers (supplies) power in a contactless manner using a magnetic field (in the present embodiment, using magnetic resonance). The contactless power supply system 100 is equipped with a power supply apparatus 10 (the primary device) and one or multiple electronic devices (secondary devices) given as power recipient devices. Herein, an electronic device 20A in the form of a mobile phone handset and an electronic device 20B in the form of a digital still camera are provided as power recipient devices, for example. However, a power recipient device is not limited to this example, and may be any electronic device able to receive power from the power supply apparatus 10 in a contactless manner.

As illustrated in FIG. 2, for example, the contactless power supply system 100 is configured such that power is transferred from the power supply apparatus 10 to the electronic devices 20A and 20B by placing the electronic devices 20A and 20B onto or in proximity to a power supply surface (transmitter surface) S1 of the power supply apparatus 10. Herein, the power supply apparatus 10 has a mat shape (or tray shape) with the surface area of the power supply surface S1 being greater than devices such as the power recipient electronic devices 20A and 20B, in consideration of the case of transferring power to multiple electronic devices 20A and 20B simultaneously or in a time division (successively).

(Exemplary Configuration of Power Supply Apparatus)

As described above, the power supply apparatus 10 is an apparatus (such as a charging tray) that transfers power to electronic devices 20A and 20B using a magnetic field. As illustrated in FIG. 3, for example, the power supply apparatus 10 is equipped with a power transmitting apparatus 11 that transfers power using power supplied from a power source 9 external to the power supply apparatus 10. The external power source 9 may be, for example, an electric utility from which power is supplied via a plug socket, otherwise called a power outlet.

The power transmitting apparatus 11 includes a transmitter 12, a high-frequency power generator circuit 13, a detector circuit 14, an impedance matching circuit 15, a controller circuit 16, and a resonant capacitor (capacitive element) C1, for example. By providing the detector circuit 14 and the controller circuit 16, the power transmitting apparatus 11 in this example takes a block configuration enabling the contactless power supply system 100 to conduct unidirectional communication using load modulation. However, the configuration is not limited thereto in cases where unidirectional communication using a technique other than load modulation or bidirectional communication is considered.

Figure 5:
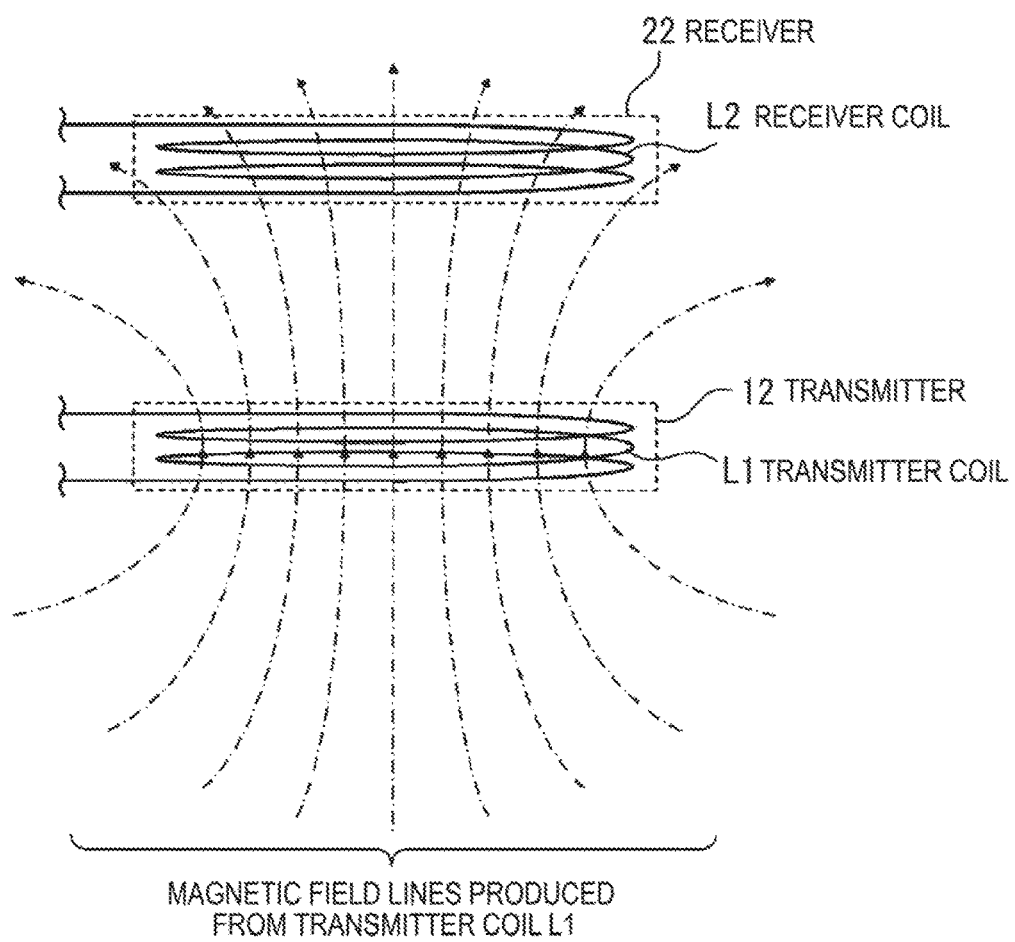
FIG. 5 is a schematic diagram of an exemplary diagrammatic configuration of a transmitter coil and a receiver coil in a contactless power supply system according to the first embodiment of the present disclosure.

The transmitter 12 includes components such as a transmitter coil (primary coil) L1 discussed later (FIG. 5). The transmitter 12 uses the transmitter coil L1 and the resonant capacitor C1 to transfer power to the electronic devices 20A and 20B (specifically, to a receiver 22 discussed later) using a magnetic field. Specifically, the transmitter 12 includes functionality for emitting a magnetic field (magnetic flux)

from the power supply surface S1 towards the electronic devices 20A and 20B. A detailed configuration of the transmitter 12 will be discussed later.

The high-frequency power generator circuit 13 is a circuit that uses power supplied from the power source 9 external to the power supply apparatus 10 to generate given high-frequency power (an AC signal) for the purpose of power transfer, for example.

The detector circuit 14 is a circuit that includes functionality for detecting (demodulating) a modulated signal from a load modulator circuit 29 discussed later. The detector circuit 14 supplies detection results to the controller circuit 16.

The impedance matching circuit 15 is a circuit that matches impedance during power transfer. In so doing, efficiency during power transfer (the transfer efficiency) is improved. Note that, depending on the configuration of components such as the transmitter coil L1 and a receiver coil L2 discussed later, or the resonant capacitors C1 and C2, it may also be configured such that the impedance matching circuit 15 is not provided. Also, if decreased transfer efficiency is not a concern, it may be configured such that the impedance matching circuit 15 is not provided.

The resonant capacitor C1 is a capacitive element constituting part of the transmitter coil L1 of the transmitter 12 as well as the LC resonator (resonant circuit), and is disposed with respect to the transmitter coil L1 so as to form an electrical series connection, parallel connection, or a combined series and parallel connection. With an LC resonator including the transmitter coil L1 and the resonant capacitor C1, resonant operation is realized at a resonant frequency (first resonant frequency) f1 whose frequency is approximately equal or near that of the high-frequency power generated in the high-frequency power generator circuit 13. The capacitance value of the resonant capacitor C1 is also set so as to obtain such a resonant frequency f1.

However, it may also be configured such that the resonant capacitor C1 is not provided if the above resonant frequency f1 is realized by resonant operation using a potential difference across the windings in the transmitter coil L1 or a parasitic capacitance component (stray capacitance component) realized by a potential difference between the transmitter coil L1 and the receiver coil L2 discussed later. Also, if decreased transfer efficiency is not a concern, it may be similarly configured such that the resonant capacitor C1 is not provided.

The controller circuit 16 is a circuit that receives detection results from the detector circuit 14 and controls components such as the high-frequency power generator circuit 13, the impedance matching circuit 15, the resonant capacitor C1, and the transmitter 12.

For example, consider the case where foreign metal is detected between the transmitter 12 and the receiver 22 by a foreign matter detecting apparatus 31 discussed later in the electronic devices 20A and 20B. At this point, the detection result from the detector circuit 14 changes due to load modulation conducted in the load modulator circuit 29, also discussed later, in the electronic devices 20A and 20B. For this reason, the controller circuit 16 in the power transmitting apparatus 11 is able to confirm the presence of foreign metal, making it possible to restrict or stop power transfer under control by the controller circuit 16. Meanwhile, the controller circuit 16 also receives detection results from the detector circuit 14 and applies pulse-width modulation control (PWM control) to the high-frequency power generator circuit 13 and switching control to the impedance matching circuit 15, the resonant capacitor C1, and the transmitter 12.

Such control by the controller circuit 16 also enables automatic control for maintaining a high transfer efficiency (power supply efficiency).

(Exemplary Configuration of Electronic Device)

Electronic devices such as stationary electronic devices typified by televisions or portable electronic devices typified by mobile phones and digital cameras, including rechargeable batteries, are applicable as the electronic devices 20A and 20B. The electronic device 20A and the electronic device 20B are provided with similar functionality with respect to power supply, and in the description hereinafter, the electronic device 20A will be described as a representative example.

As illustrated in FIG. 3, for example, the electronic device 20A is equipped with a power receiving apparatus 21 and a load 27 that performs given action (action that elicits functionality as an electronic device) on the basis of power supplied from the power receiving apparatus 21. The electronic device 20A is also equipped with a foreign matter detecting apparatus 31 for detecting the presence of foreign metal between (in the gap between) the transmitter 12 and the receiver 22.

Hereinafter, the power receiving apparatus 21 will be described.

The power receiving apparatus 21 includes a receiver 22, a resonant capacitor (capacitive element) C2, an impedance matching circuit 23, a rectifier circuit 24, a voltage stabilizer circuit 25, a controller circuit 26, a battery 28, and a load modulator circuit 29. By providing the load modulator circuit 29 and the controller circuit 26, the power receiving apparatus 21 in this example takes a block configuration enabling the contactless power supply system 100 to conduct unidirectional communication using load modulation. However, the configuration is not limited thereto in cases where unidirectional communication using a technique other than load modulation or bidirectional communication is considered.

The receiver 22 includes components such as a receiver coil (secondary coil) L2 discussed later (FIG. 5). The receiver 22 includes functionality for using the receiver coil L2 and the resonant capacitor C2 to receive power transferred from the transmitter 12 in the power supply apparatus 10. A detailed configuration of the receiver 22 will be discussed later.

The resonant capacitor C2 is a capacitive element constituting part of the receiver coil L2 of the receiver 22 as well as the LC resonator (resonant circuit), and is disposed with respect to the receiver coil L2 so as to form an electrical series connection, parallel connection, or a combined series and parallel connection. With an LC resonator including the receiver coil L2 and the resonant capacitor C2, resonant operation is realized at a resonant frequency (second resonant frequency) f2 whose frequency is approximately equal or near that of the high-frequency power generated in the high-frequency power generator circuit 13 of the power transmitting apparatus 11. In other words, the LC resonator including the transmitter coil L1 and the resonant capacitor C1 in the power transmitting apparatus 11 and the LC resonator including the receiver coil L2 and the resonant capacitor C2 in the power receiving apparatus 21 resonate with each other at approximately equal resonant frequencies (f1≈f2). The capacitance value of the resonant capacitor C2 is also set so as to obtain such a resonant frequency f2.

However, it may also be configured such that the resonant capacitor C2 is also not provided if the above resonant frequency f1 is realized by resonant operation using a potential difference across the windings in the receiver coil L2 or a parasitic capacitance component realized by a potential difference between the transmitter coil L1 and the receiver coil L2. Also, if decreased transfer efficiency is not a concern, it may also be configured such that the resonant frequency f2 and the resonant frequency f1 differ from each other (f2≠f1), and the resonant capacitor C2 is not provided.

The impedance matching circuit 23 is a circuit that matches impedance during power transfer, similarly to the impedance matching circuit 15 in the above power transmitting apparatus 11. Note that, depending on the configuration of components such as the transmitter coil L1 and the receiver coil L2 discussed later, or the resonant capacitors C1 and C2, it may also be configured such that the impedance matching circuit 23 is also not provided. Also, if decreased transfer efficiency is not a concern, it may be similarly configured such that the impedance matching circuit 23 is also not provided.

The rectifier circuit 24 is a circuit that rectifies the power (AC power) supplied from the receiver 22 to generate direct current (DC) power. Note that a smoothing circuit (not illustrated) for smoothing rectified power is often provided between the rectifier circuit 24 and the voltage stabilizer circuit 25 discussed later.

The voltage stabilizer circuit 25 is a circuit that conducts given voltage stabilization on the basis of DC power supplied from the rectifier circuit 24, and charges the battery 28 or a battery (not illustrated) in the load 27.

The battery 28 stores power in response to being charged by the voltage stabilizer circuit 25, and may be realized using a rechargeable battery (secondary cell) such as a lithium-ion battery, for example. Note that the battery 28 may also be omitted in cases where only the battery in the load 27 is used, for example.

The load modulator circuit 29 is a circuit for applying load modulation, and changes in the power state due to load modulation may be detected with the detector circuit 14 in the power transmitting apparatus 11. In other words, if given the load modulator circuit 29 and the controller circuit 26 discussed later, it becomes possible to transmit information in the power receiving apparatus 21 to the power transmitting apparatus 11 without providing a special communication apparatus in the electronic device 20A.

The controller circuit 26 is a circuit for controlling charging operation with respect to the battery 28 or the battery (not illustrated) in the load 27. The controller circuit 26 is also a circuit for controlling load modulation in the load modulator circuit 29, and applies control enabling the power transmitting apparatus 11 to recognize that foreign metal has been detected by having changes in the power state due to such load modulation be detected with the detector circuit 14 in the power transmitting apparatus 11. Additionally, in the case where the foreign matter detecting apparatus 31 discussed later in the electronic device 20A detects that foreign metal is present between the transmitter 12 and the receiver 22, it is also possible for the controller circuit 26 to apply charging control to restrict or stop power transfer to the power receiving apparatus 21 in the electronic device 20A.

Hereinafter, the foreign matter detecting apparatus 31 will be described. The foreign matter detecting apparatus 31 includes a detector coil L3, a resonant capacitor C3, a foreign matter detector circuit 32, and a controller circuit 33. As an example, the foreign matter detector circuit 32 and the controller circuit 33 may constitute a detector.

The detector coil L3 is an example of a magnetic coupling element for detecting foreign metal, and is provided separately from the transmitter coil L1 and the receiver coil L2. Further details will be discussed later (FIGS. 4A, 4B, 4C, 6A, 6B, 7A, 7B, 14-19, 20A, 20B, 20C, 21A, 21B, 21C, 22A and 22B).

Figure 4A:
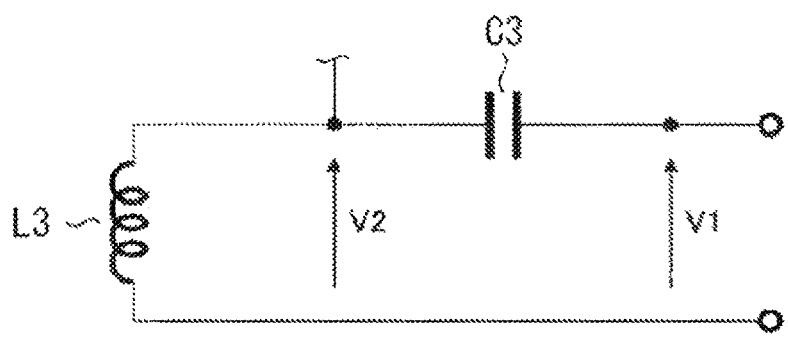
FIGS. 4A to 4C are circuit diagrams illustrating exemplary configurations of a resonant circuit.
Figure 4B:
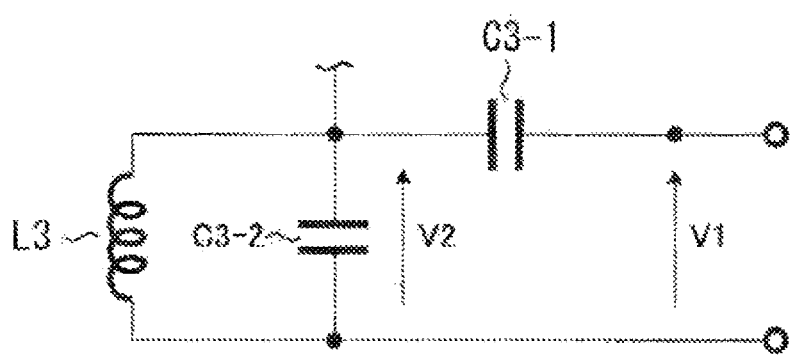
Figure 4C:
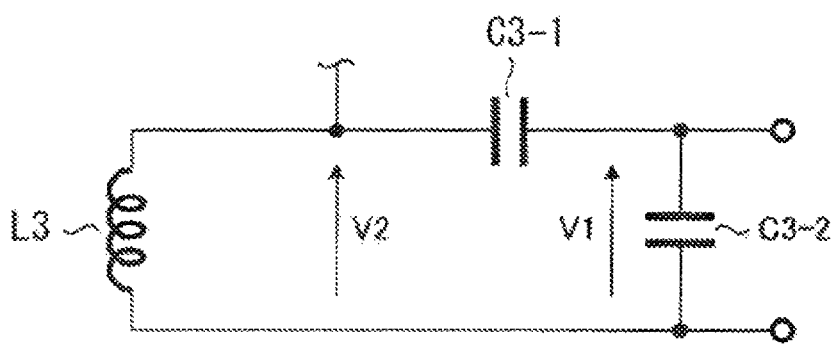

The resonant capacitor C3 is a capacitor connected to the detector coil L3 in an electrical series configuration (see FIG. 4A), or a capacitor connected to the detector coil L3 in a combined electrical series and parallel configuration (resonant capacitors C3-1 and C3-2) (see FIGS. 4B and 4C). By connecting the resonant capacitor C3, the detector coil L3 resonates at a given frequency f3 (LC resonance).

Note that in the case of computing the Q factor of the LC resonator (resonant circuit) from the voltage ratio as discussed later, it is desirable to connect at least one resonant capacitor C3 to the detector coil L3 in series (see FIGS. 4A, 4B, and 4C). However, in the case of computing the Q factor of the LC resonator with a technique other than voltage ratio, such as with a width at half maximum (WHM) method, the resonant capacitor C3 may be connected to the detector coil L3 in an electrical parallel configuration (not illustrated).

The foreign matter detector circuit 32 is a circuit for measuring the Q factor of the detector coil L3 or the Q factor of the LC resonator including the detector coil L3 and the resonant capacitor C3 by using an AC signal whose frequency (f3, where f3≠f2 and f3≠f2) differs from the frequencies (f1 and f2, where f1≈f2) of the AC signals flowing through the transmitter coil L1 and the receiver coil L2.

The Q factor of the detector coil L3 or the Q factor of the LC resonator including the detector coil L3 and the resonant capacitor C3 may be computed by measuring voltage values at the two locations (the voltage value V1 and the voltage value V2) illustrated in FIGS. 4A, 4B, and 4C as described earlier with the foreign matter detector circuit 32, and then taking their ratio (V2/V1), for example.

Also, if the frequency characteristics related to properties such as the impedance and admittance are able to be measured with the foreign matter detector circuit 32, it is also possible to compute the Q factor of the detector coil L3 or the LC resonator from the ratio of the peak frequency at which the frequency characteristics reach a peak versus the frequency width where that peak value is halved (WHM) (thus, peak frequency/WHM).

Additionally, it is also possible to calculate the Q factor from the ratio of the real part versus the imaginary part of the impedance of the resonant circuit. The real part and the imaginary part of the impedance may be computed using an auto-balancing bridge circuit and a vector ratio detector, for example.

The controller circuit 33 is a circuit that controls the foreign matter detector circuit 32, while also determining the presence of foreign metal between (in the gap between) the transmitter 12 and the receiver 22 from the measurement results by the foreign matter detector circuit 32. The controller circuit 33 is also a circuit for transmitting the determination result to the controller circuit 26 of the power receiving apparatus 21. The controller circuit 33 may, for example, compare a measured Q factor to a threshold value saved in memory (not illustrated) in advance, and determine that foreign metal is present near the detector coil in the case where the measured Q factor is less than the threshold value.

[Detailed Exemplary Configuration of Transmitter And Receiver]

FIG. 5 is a schematic illustration of an exemplary diagrammatic configuration of the transmitter 12 and the receiver 22 in a contactless power supply system according to the first embodiment of the present disclosure.

The transmitter 12 includes at least one (in this case, one) transmitter coil L1, and the receiver 22 includes at least one (in this case, one) receiver coil L2. It is possible for the transmitter coil L1 and the receiver coil L2 to be magnetically coupled to each other. Note that it may also be configured such that the transmitter 12 and the receiver 22 includes one or multiple coils or one or multiple LC resonators including coils and capacitors in addition to the transmitter coil L1 and the receiver coil L2.

These coils (the transmitter coil L1 and the receiver coil L2) are not limited to being open coils (conductive coils) shaped like conductive wire (material) wound multiple times, but may also be open loops (conductive loops) shaped like conductive wire wound one time.

Furthermore, the coil or loop used as such a conductive coil or conductive loop may be a coil (wound coil) or loop (wound loop) in which conductive wire is wound, or a coil (patterned coil) or loop (patterned loop) formed by a conductive pattern on a printed substrate (printed circuit board) or flexible printed substrate (flexible printed circuit board), for example. Also, it is possible to form such a patterned coil and patterned loop by printing or depositing conductive material, or by machining a conductive metal plate or sheet, for example.

FIG. 5 simultaneously illustrates an exemplary distribution of magnetic field lines produced from the transmitter coil L1 at a given phase. As described above, the transmitter coil L1 is a coil for transferring power using magnetic flux (lines of magnetic force; a magnetic field). In other words, the transmitter coil L1 is a coil for producing magnetic flux (lines of magnetic force; a magnetic field). Meanwhile, the receiver coil L2 is a coil for receiving power from the magnetic flux (lines of magnetic force; a magnetic field) transferred from the transmitter 12.

[Detailed Exemplary Configuration of Detector Coil]

Figure 6A:
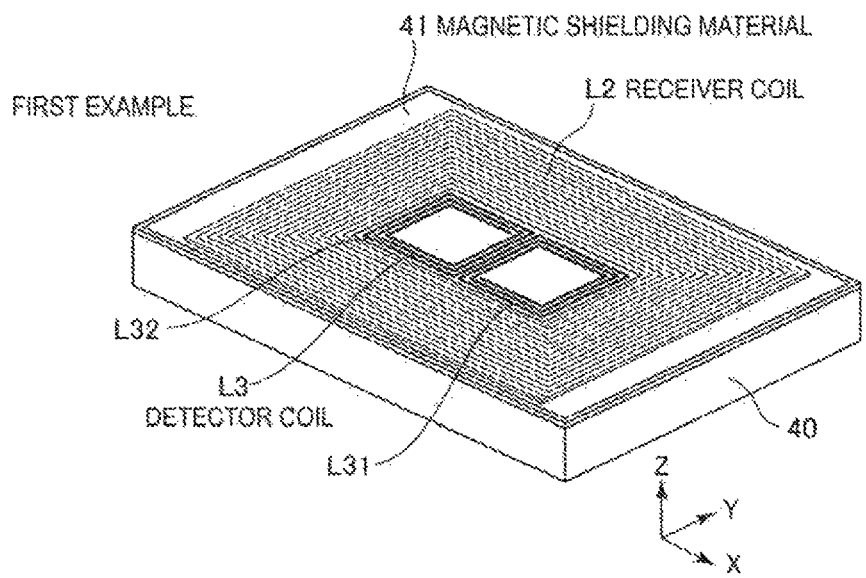
FIG. 6A and FIG. 6B are explanatory diagrams illustrating an exemplary detailed configuration of a detector coil and receiver coil according to the first embodiment of the present disclosure, where
Figure 6B:
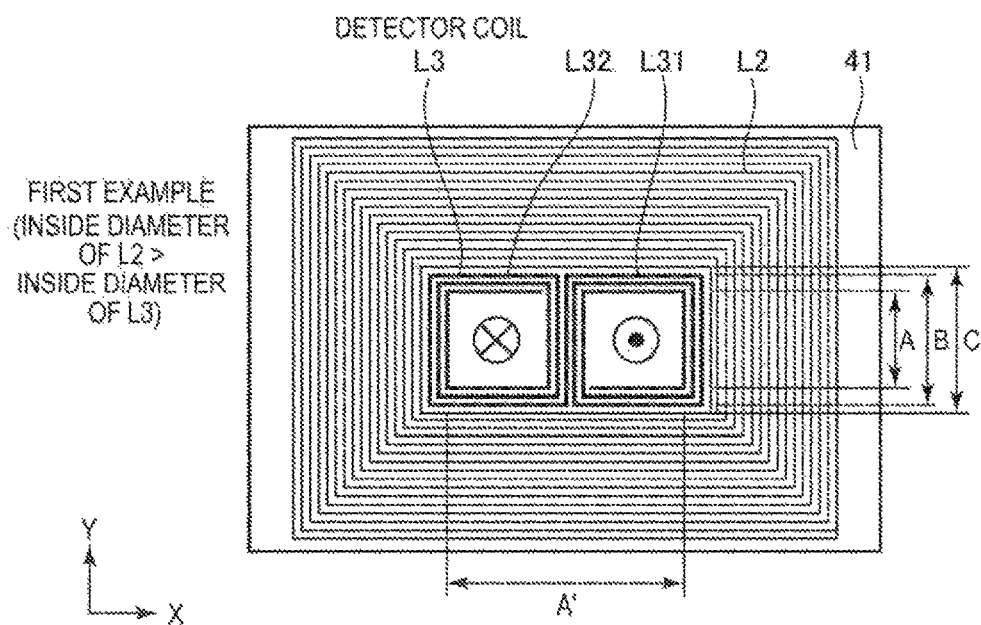

FIG. 6A and FIG. 6B are illustration of an exemplary detailed configuration of the detector coil L3 and the receiver coil L2 according to the first embodiment of the present disclosure, where FIG. 6A is an exemplary perspective view configuration and FIG. 6B is an exemplary plan view configuration (exemplary X-Y plan view configuration).

The receiver coil L2 illustrated in FIG. 6A and FIG. 6B is a spiral-shaped coil. In order to effectively raise the magnetic coupling between the transmitter coil L1 and the receiver coil L2, it is desirable for the transmitter coil L1 and the receiver coil L2 to be spiral-shaped coils, helical coils, or coils with a combined spiral and helical shape, for example. However, the transmitter coil L1 and the receiver coil L2 are not limited thereto.

Also, the detector coil L3 illustrated in FIG. 6A and FIG. 6B is a figure 8-shaped coil realized by a combination of a spiral-shaped coil L31 and a spiral-shaped coil L32 that distributes magnetic flux of approximately the opposite orientation of the orientation of the magnetic flux from the coil L31. Although details will be discussed later, if the detector coil L3 is simply a spiral-shaped coil, helical coil, or a coil with a combined spiral and helical shape, foreign metal detection accuracy may greatly decrease. For this reason, it is desirable for the detector coil L3 to be a coil able to distribute magnetic flux (magnetic field lines; a magnetic field) over a surface with approximately opposing orientations, such as a figure 8-shaped, square grid-shaped, or lattice-shaped coil as discussed later.

Although details will likewise be discussed later, using a detector coil with such a shape yields advantages such as enabling decreased magnetic flux leakage from the detector coil, decreased change in the electrical properties (such as the Q factor and L value) of the detector coil due to external factors, and a decrease in unwanted noise occurring in the detector coil. For this reason, it is possible to greatly improve foreign metal detection accuracy.

Furthermore, the coil or loop used as the detector coil L3 may be a coil (wound coil) or loop (wound loop) in which conductive wire is wound, or a coil (patterned coil) or loop (patterned loop) formed by a conductive pattern on a printed substrate (printed circuit board) or flexible printed substrate (flexible printed circuit board), for example. Also, it is possible to form such a patterned coil and patterned loop by printing or depositing conductive material, or by machining a conductive metal plate or sheet, for example.

Figure 9:
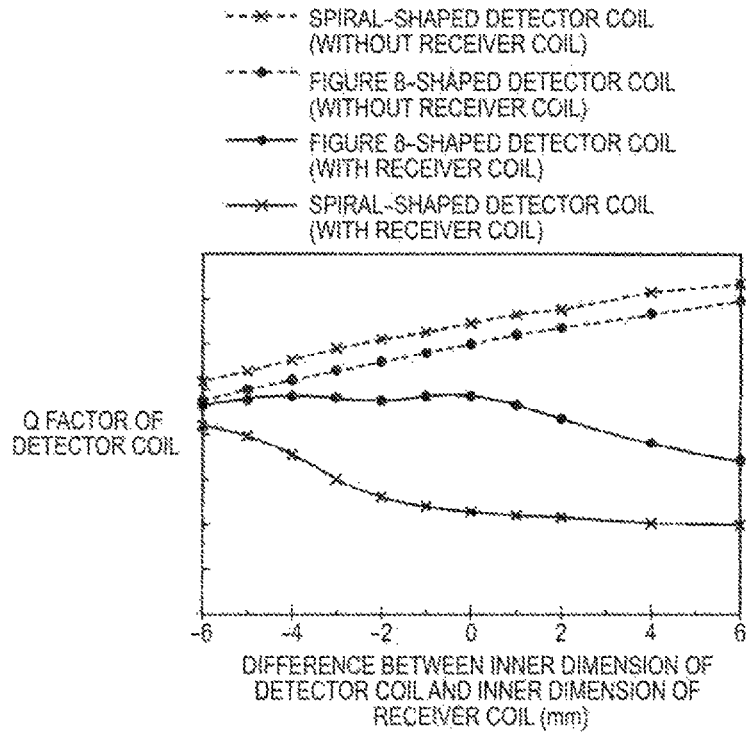
FIG. 9 is a graph of examples illustrating to what degree the detector coil Q factor changes depending on the presence or absence of a receiver coil in the case of modifying the inner dimension of the detector coil.

Also, while the receiver coil L2 and the detector coil L3 may be disposed in the same plane, the receiver coil L2 and the detector coil L3 may also be disposed in different planes. However, for the sake of the packaging area with respect to the electronic device 20A (20B), in many cases it is desirable to form the receiver 22 (receiver coil L2) and the detector coil L3 in the same plane. In the example in FIG. 6A and FIG. 6B, the receiver coil L2 and the detector coil L3 are not disposed in the same plane for the sake of comparison as illustrated in FIG. 9, discussed later.

Additionally, in FIG. 6A and FIG. 6B, the inner dimension (the dimension of the innermost perimeter) of the detector coil L3 is smaller than the inner dimension C (the dimension of the innermost perimeter) of the receiver coil L2, and the outer dimension B (the dimension of the outermost perimeter) of the detector coil L3 is smaller than the inner dimension C (the dimension of the innermost perimeter) of the receiver coil L2. Although details will be discussed later, such a configuration maximally raises the foreign metal detection accuracy. Obviously, however, the configuration is not limited thereto in applications where foreign metal detection accuracy is not demanded.

Note that although FIG. 6A and FIG. 6B compared the inner dimension A and the outer dimension B along the shorter edge of the figure 8-shaped detector coil L3 to the inner dimension C along the shorter edge of the receiver coil L2, the dimensions may also be compared using the respective inner dimensions and outer dimensions along the longer edge (such as the inner dimension A' along the longer edge of the detector coil L3, for example). It is further desirable if the inner dimension and outer dimension along both the shorter edge and the longer edge of the detector coil are smaller than the inner dimensions along both the shorter edge and the longer edge of the receiver coil. Obviously, however, the configuration is not limited thereto in applications where foreign metal detection accuracy is not demanded.

Additionally, although it is desirable for the detector coil L3 to be electrically insulated from (i.e., not connected to an electrical contact point or other element in) the transmitter 12 (transmitter coil L1) and the receiver 22 (receiver coil L2), the configuration is not limited thereto.

Note that in FIG. 6A and FIG. 6B, magnetic shielding material 41 is disposed between the housing 40 of the electronic device, and the receiver coil L2 and detector coil L3. The magnetic shielding material 41 is provided for the purpose of decreasing magnetic flux leakage from the receiver coil L2 and raising the Q factors of the receiver coil L2 and the detector coil L3, but may also be omitted as appropriate. The magnetic shielding material 41 herein may be realized with magnetic material such as ferrite, conductive metal such as metal, or a combination of magnetic material and conductive metal, for example.

Figure 7A:
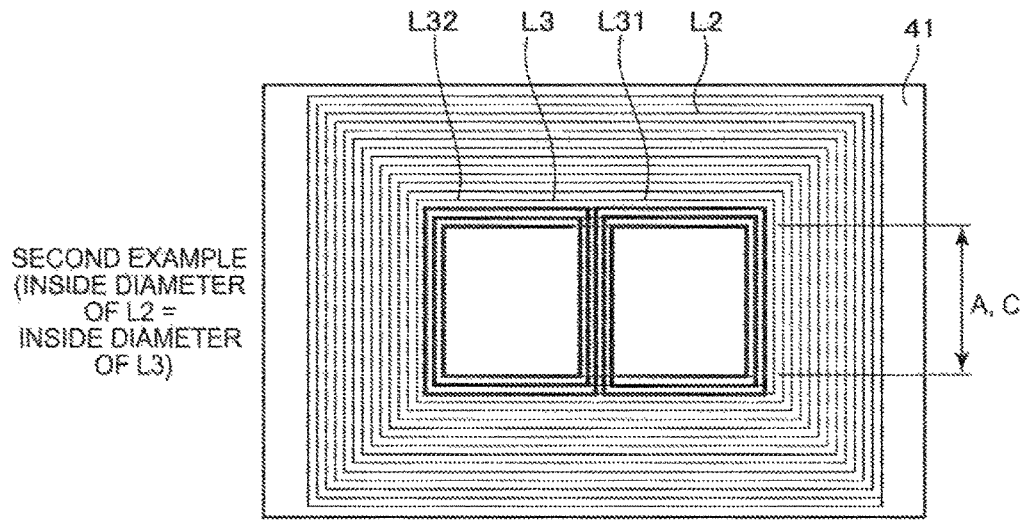
FIG. 7A and FIG. 7B are plan views illustrating an exemplary detailed configuration of a detector coil and receiver coil according to the first embodiment of the present disclosure, where
Figure 7B:
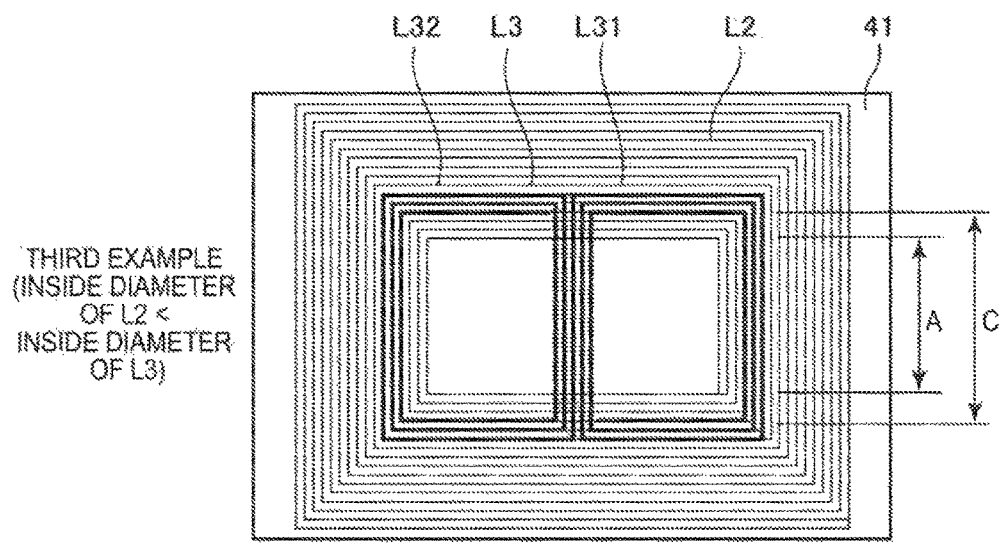

FIG. 7A and FIG. 7B illustrate different examples of the difference between the inner dimension of the detector coil L3 and the inner dimension of the receiver coil L2 in the exemplary detailed configuration of the detector coil L3 and the receiver coil L2 in FIG. 6A and FIG. 6B.

FIG. 7A illustrates an exemplary detailed configuration of the detector coil L3 and the receiver coil L2 in the case where the difference between the inner dimension A of the detector coil L3 and the inner dimension C of the receiver coil L2 is 0 mm. Additionally, FIG. 7B illustrates an exemplary detailed configuration of the detector coil L3 and the receiver coil L2 in the case where the difference between the inner dimension A of the detector coil L3 and the inner dimension C of the receiver coil L2 is +4 mm.

[Action And Advantages of Contactless Power Supply System]

(1. Summary of Overall Operation)

In the power supply apparatus 10 of the contactless power supply system 100, the high-frequency power generator circuit 13 supplies given high-frequency power (an AC signal) for transferring power to the transmitter coil L1 and the resonant capacitor C1 (LC resonator) in the transmitter 12. In so doing, a magnetic field (magnetic flux) is produced in the transmitter coil L1 in the transmitter 12. At this point, if an electronic device 20A given as a power recipient (charging target) is placed (or brought near) the top surface (power supply surface S1) of the power supply apparatus 10, the transmitter coil L1 in the power supply apparatus 10 and the receiver coil L2 in the electronic device 20A come into proximity near the power supply surface S1.

In this way, if a receiver coil L2 is placed near a transmitter coil L1 producing a magnetic field (magnetic flux), electromotive force, induced by the magnetic flux produced from the transmitter coil L1, is produced in the receiver coil L2. In other words, the transmitter coil L1 and the receiver coil L2 are respectively linked by electromagnetic induction or magnetic resonance, and a magnetic field is produced. In so doing, power (indicated as the contactless power supply P1 in FIG. 3) is transferred from the transmitter coil L1 (primary coil; power supply apparatus 10; transmitter 12) to the receiver coil L2 (secondary coil; electronic device 20A; receiver 22). At this point, resonant operation using the transmitter coil L1 and the resonant capacitor C1 is conducted in the power supply apparatus 10 (at a resonant frequency f1), while resonant operation using the receiver coil L2 and the resonant capacitor C2 is conducted in the electronic device 20A (at a resonant frequency f2, where f2≈f1).

Thereupon, AC power received by the receiver coil L2 in the electronic device 20A is supplied to the rectifier circuit 24 and the voltage stabilizer circuit 25, and the following charging operation is performed. Namely, after the AC power is converted into given DC power by the rectifier circuit 24, voltage stabilization based on the DC power is performed by the voltage stabilizer circuit 25, and the battery 28 or a battery (not illustrated) in the load 27 is charged. In so doing, charging operation based on power received by the receiver 22 is performed in the electronic device 20A.

In other words, in the present embodiment, a terminal connection to an AC adapter, for example, is unnecessary when charging the electronic device 20A, and charging may be easily initiated (contactless power supply may be performed) by simply placing the electronic device 20A onto (or in proximity to) the power supply surface S1 of the power supply apparatus 10. This leads to a reduced burden on the user.

Meanwhile, in the foreign matter detecting apparatus 31 of the electronic device 20A, the Q factor of a detector coil L3 or an LC resonator including the detector coil L3 and a resonant capacitor C3 is measured using an AC signal whose frequency (f3, where f3≠f2 and f3≠f2) differs from the frequencies (f1 and f2) of the AC signals flowing through the transmitter coil L1 and the receiver coil L2. The foreign matter detecting apparatus 31 is also able to determine the presence of foreign metal between (in the gap between) the transmitter 12 and the receiver 22 from the magnitude of change in this Q factor.

Subsequently, a determination result by the foreign matter detecting apparatus 31 which indicates the presence or absence of foreign metal is transmitted from the power receiving apparatus 21 in the electronic device 20A to the power transmitting apparatus 11 in the power supply apparatus 10 by a communication technique such as load modulation.

Furthermore, in the case where the foreign matter detecting apparatus 31 detects the presence of foreign metal between (in the gap between) the transmitter 12 and the receiver 22, control for restricting or stopping power transfer is applied by the controller circuit 16 in the power transmitting apparatus 11 or the controller circuit 26 in the power receiving apparatus 21, for example. As a result, it may be possible to preemptively avoid heat or fire produced in the foreign metal, as well as malfunction or damage to the contactless power supply system.

(2. Action of Detector Coil)

Next, action of the detector coil L3 given as a characteristic feature of the present embodiment will be described in detail and in comparison to comparative examples (examples of the related art).

(2.1 Case of Detector Coil According to Comparative Examples)

Figure 8A:
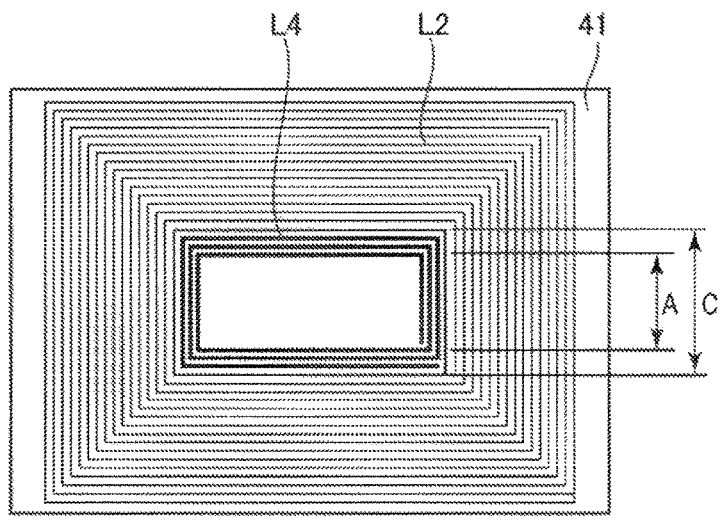
FIG. 8A and FIG. 8B are plan views illustrating an exemplary detailed configuration of a detector coil and receiver coil according to a first comparative example, where
Figure 8B:
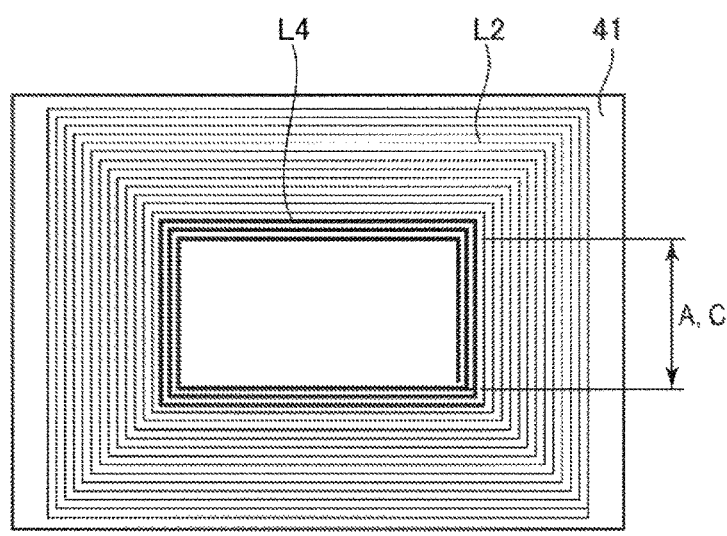

FIG. 8A and FIG. 8B are plan views illustrating an exemplary detailed configuration of a detector coil and receiver coil according to comparative examples. FIG. 8A illustrates an exemplary detailed configuration (exemplary X-Y plan view configuration) of a detector coil L4 according to a first comparative example and the receiver coil L2, in the case where the difference between the inner dimension of the detector coil L4 and the inner dimension of the receiver coil L2 is −4 mm. FIG. 8B illustrates an exemplary detailed configuration (exemplary X-Y plan view configuration) of a detector coil L4 according to a second comparative example and the receiver coil L2, in the case where the difference between the inner dimension of the detector coil L4 and the inner dimension of the receiver coil L2 is 0 mm.

Unlike a detector coil L3 according to an embodiment of the present disclosure described earlier, these detector coils L4 are simple spiral-shaped coils.

First, data related to the detector coil Q factor is acquired by applying electromagnetic field analysis to an analysis model of a detector coil and a receiver coil like those illustrated in FIGS. 8A and 8B (see FIG. 9). The graph in FIG. 9 illustrates to what degree the Q factor of the detector coil L4 changes depending on the presence or absence of the receiver coil L2 in the case of modifying the inner dimension of the detector coil L4. However, when modifying the inner dimension of the detector coil L4, factors such as the conductive wire type, thickness, width, and the length of the gap between conductive wires constituting the detector coil L4 are not modified.

FIG. 8A is an exemplary detailed configuration of a detector coil and a receiver coil in the case where the difference between the inner dimension of the detector coil and the inner dimension of the receiver coil is −4 mm in the graph in FIG. 9. Also, FIG. 8B is an exemplary detailed configuration of a detector coil and a receiver coil in the case where the difference between the inner dimension of the detector coil and the inner dimension of the receiver coil is 0 mm in FIG. 9.

FIG. 9 demonstrates that in the case of using a spiral-shaped detector coil L4, the Q factor of the detector coil L4 changes greatly depending on whether or not the receiver coil L2 is present. In other words, FIG. 9 demonstrates that the Q factor of the detector coil L4 decreases greatly when the receiver coil L2 is present. This indicates that in the case of using a spiral-shaped detector coil L4, there is significant magnetic flux leakage from the detector coil L4, and the electrical properties (such as the Q factor and L value) of the detector coil L4 change greatly due to external factors (such as the metal material or magnetic material constituting the transmitter coil L1, the receiver coil L2, the magnetic shielding material 41, the power supply apparatus 10, and the electronic device 20A (20B)).

Stated differently, FIG. 9 demonstrates that foreign metal detection accuracy is greatly decreased in the case of using a spiral-shaped coil as the detector coil. Furthermore, FIG. 9 also demonstrates that as the inner dimension A of the detector coil L4 becomes smaller with respect to the inner dimension C of the receiver coil L2 (for example, if the difference between the detector coil inner dimension A and the receiver coil inner dimension C becomes less than or equal to 0 mm), the amount of decrease in the Q factor of the detector coil L4 due to the presence of the receiver coil L2 also becomes smaller (see the right side of FIG. 9).

(2.2 Case of Detector Coil According to First Embodiment)

In contrast, in the first embodiment of the present disclosure, a figure 8-shaped detector coil L3 is used, as illustrated in FIGS. 6A, 6B, 7A and 7B. All other parameters are basically the same as those of the first comparative example and the second comparative example.

Similarly to the case of the above comparative example, data related to the detector coil Q factor is acquired by applying electromagnetic field analysis to an analysis model of a detector coil and a receiver coil like those illustrated in FIGS. 6A, 6B, 7A, and 7B (see FIG. 9). FIG. 9 illustrates to what degree the Q factor of the detector coil L3 changes depending on the presence or absence of the receiver coil L2 in the case of modifying the inner dimension of the detector coil L3. However, when modifying the inner dimension of the detector coil L3, factors such as the conductive wire type, thickness, width, and the length of the gap between conductive wires constituting the detector coil L3 are not modified.

FIG. 9 demonstrates that in the case of using a figure 8-shaped detector coil L3, although the Q factor of the detector coil L3 does change slightly depending on whether or not the receiver coil L2 is present, the magnitude of that change is significantly smaller than in the case of using the spiral-shaped detector coil L4. In other words, FIG. 9 demonstrates that although the Q factor of the detector coil L3 does change slightly due to the presence of the receiver coil L2, the magnitude of that change is significantly smaller than in the case of using the spiral-shaped detector coil L4. This indicates that for the figure 8-shaped detector coil L3, there is less magnetic flux leakage from the detector coil L3, and the electrical properties (such as the Q factor and L value) of the detector coil L3 change less due to external factors (such as the metal material or magnetic material constituting the transmitter coil L1, the receiver coil L2, the magnetic shielding material 41, the power supply apparatus 10, and the electronic device 20A (20B)) compared to the spiral-shaped detector coil L4.

Stated differently, FIG. 9 demonstrates that in the case of using a figure 8-shaped coil as the detector coil, foreign metal detection accuracy is greatly improved compared to the case of using a spiral-shaped coil. Furthermore, FIG. 9 also demonstrates that as the inner dimension A of the detector coil L3 becomes smaller with respect to the inner dimension C of the receiver coil L2 (for example, if the difference between the detector coil inner dimension A and the receiver coil inner dimension C becomes less than or equal to 0 mm), the amount of decrease in the Q factor of the detector coil L3 due to the presence of the receiver coil L2 also becomes smaller.

In addition, FIG. 9 demonstrates that the Q factor of the detector coil L3 is greatest (maximized) in the case where the difference between the detector coil inner dimension A and the receiver coil inner dimension C is −4 mm, and in the case where the difference between the detector coil inner dimension A and the receiver coil inner dimension C is 0 mm. In other words, FIG. 9 demonstrates that it is desirable for the inner dimension A of the detector coil L3 to be smaller than the inner dimension C of the receiver coil L2.

Also, since the difference in the Q factor of the detector coil L3 depending on whether or not the receiver coil L2 is present becomes smaller as the inner dimension A of the detector coil L3 becomes smaller with respect to the inner dimension C of the receiver coil L2, FIG. 9 demonstrates that it is desirable for the outer dimension B of the detector coil L3 also to be smaller than the inner dimension C of the receiver coil L2. However, the configuration is not limited thereto in the case where it is desirable to extend the foreign metal detection range even if the foreign metal detection accuracy drops.

(2.3 Distribution of Magnetic Field Lines in Detector Coil)

The distribution of magnetic field lines in a detector coil will now be described with reference to FIGS. 10A and 10B.

Figure 10A:
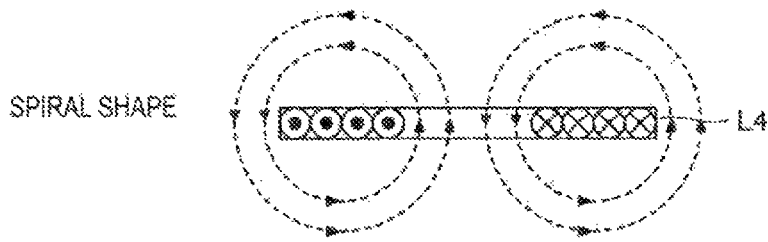

FIG. 10A is a diagrammatic cross-section view regarding a spiral-shaped coil (the detector coil L4, for example) at a given time (phase) and the distribution of magnetic field lines produced from that coil. FIG. 10B is a diagrammatic cross-section view regarding a figure 8-shaped coil (the detector coil L3, for example) at a given time (phase) and the distribution of magnetic field lines from that coil.

Figure 10B:
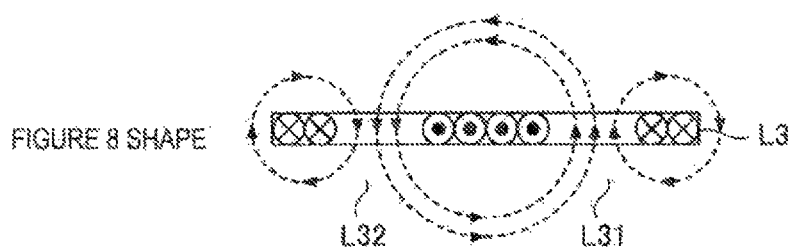
FIG. 10B is a diagrammatic cross-section view regarding a figure 8-shaped coil according to an embodiment of the present disclosure and the distribution of magnetic field lines from that coil.

As illustrated in FIGS. 10A and 10B, the distribution of magnetic field lines differs greatly between a spiral-shaped coil and a figure 8-shaped coil. The figure 8-shaped coil discussed above is configured to be able to distribute magnetic flux (magnetic field lines; a magnetic field) over a surface such that the magnetic flux from the two coils (the coils L31 and L32, for example) constituting the figure 8-shaped coil have approximately opposing orientations. As a result, in the figure 8-shaped coil, magnetic field lines are distributed so as to form a loop inside the coil. In other words, in the figure 8-shaped coil, the magnetic field lines are less likely to be distributed farther compared to a spiral-shaped coil.

For this reason, using the figure 8-shaped detector coil L3 yields less magnetic flux leakage from the detector coil L3, and the electrical properties (such as the Q factor and L value) of the detector coil L3 change less due to external factors (such as the metal material or magnetic material constituting the transmitter coil L1, the receiver coil L2, the magnetic shielding material 41, the power supply apparatus 10, and the electronic device 20A (20B)) compared to the spiral-shaped detector coil L4.

(2.4 Voltage Produced in LC Resonator)

Figure 11A:
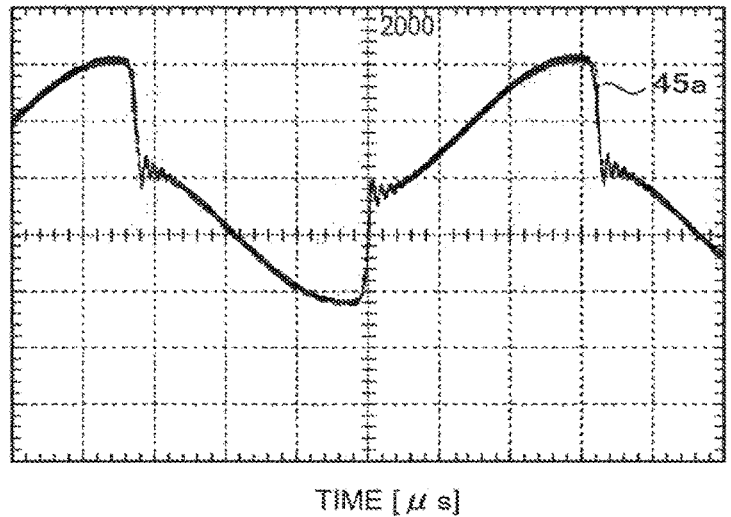

FIG. 11A illustrates a waveform 45a of voltage produced in an LC resonator including the detector coil L4 and the resonant capacitor C3 by causing actual contactless power supply operation using the power transmitting apparatus 11 and the power receiving apparatus 21, in the case where the detector coil L4 is provided inside the receiver coil L2 as illustrated in FIG. 8A.

In an actual contactless power supply system 100, voltage values (V1 and V2) are measured at two locations in an LC resonator including the detector coil L4 and the resonant capacitor C3 using an AC signal whose frequency (f3, where f3≠f2 and f3 f2) differs from the frequencies (f1 and f2, where f1≈f2) of the AC signals flowing through the transmitter coil L1 and the receiver coil L2. The Q factor is then calculated from the ratio of these two voltage values.

However, FIG. 11A demonstrates that in the case of using the spiral-shaped detector coil L4, an extremely large voltage unnecessary for foreign matter detection is produced due to the contactless power supply frequencies (f1 and f2). In the example in FIG. 11A, the voltage waveform 45a has an effective value of 690 mV, and a peak-to-peak (p-p) value of 2.25 V.

This voltage becomes a large source of unwanted noise when measuring voltage values at two locations in the LC resonator including the detector coil L4 and the resonant capacitor C3. In other words, in the case of using the spiral-shaped detector coil L4, the foreign metal detection accuracy decreases greatly due to this unwanted noise.

Figure 11B:
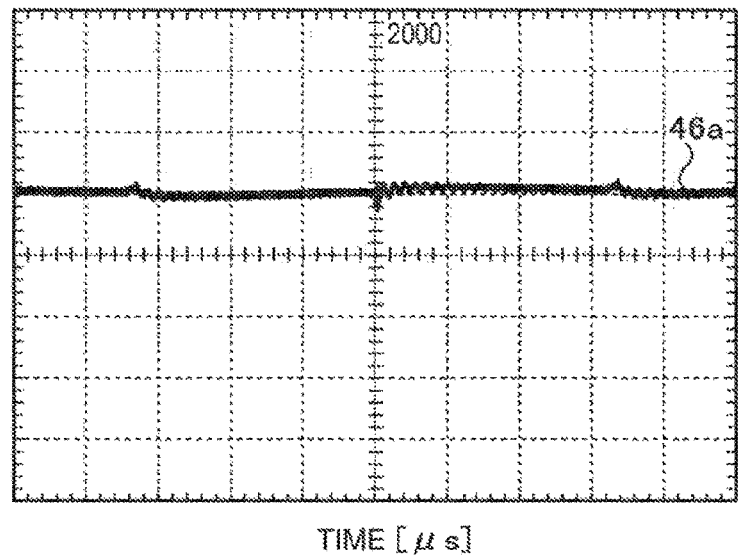
FIG. 11B is a waveform diagram illustrating an example of a waveform of voltage (voltage waveform) produced in an LC resonator including a detector coil and a resonant capacitor C3 in the case where a figure 8-shaped detector coil is disposed inside the receiver coil illustrated in FIG. 6B.

Meanwhile, FIG. 11B illustrates a waveform 46a of voltage produced in an LC resonator including the detector coil L3 and the resonant capacitor C3 by causing actual contactless power supply operation using the power transmitting apparatus 11 and the power receiving apparatus 21, in the case where the detector coil L3 is provided inside the receiver coil L2 as illustrated in FIG. 6A.

FIG. 11B demonstrates that, compared to the case of using the spiral-shaped detector coil L4, almost no voltage is produced due to the contactless power supply frequencies (f1 and f2, where f1≈f2) in the case of using the figure 8-shaped detector coil L3. In the example in FIG. 11B, the voltage waveform 46a has an effective value of 27.7 mV, and a peak-to-peak (p-p) value of 390 mV.

In an actual contactless power supply system 100, voltage values are measured at two locations in an LC resonator including the detector coil L3 and the resonant capacitor C3 using an AC signal whose frequency (f3, where f3 ≠f1 and f3 f2) differs from the frequencies (f1 and f2) of the AC signals flowing through the transmitter coil and the receiver coil. The Q factor is then calculated from the ratio of these two voltage values. In other words, since there is little unwanted noise, it can be said that using the figure 8-shaped detector coil L3 has a much higher foreign metal detection accuracy than the case of using the spiral-shaped detector coil L4.

Note that in the case where magnetic flux produced from the transmitter coil L1 or the receiver coil L2 passes through a spiral-shaped coil, the exiting magnetic flux changes according to time (phase). Thus, electromotive force attempting to make current flow in a direction opposing such change is induced in the spiral-shaped coil (see Faraday's law of induction and Lenz's law).

Meanwhile, in the case where magnetic flux produced from the transmitter coil L1 or the receiver coil L2 passes through a figure 8-shaped coil, magnetic flux respectively passes through the two coils constituting the figure 8-shaped coil (the coils L31 and L32 in FIG. 6B) in approximately the same direction. However, since the two coils constituting the figure 8-shaped coil are electrically connected such that their winding directions differ, the electromotive force produced in the coils cancel each other out in the case where magnetic flux passes through the two coils in approximately the same direction, and thus electromotive force like that of a spiral-shaped coil is not produced when observing the figure 8-shaped coil overall. For this reason, a figure 8-shaped coil yields the advantage of little unwanted noise as discussed above.

However, if the magnetic flux passing through the two coils constituting a figure 8-shaped coil greatly differ from each other, a large level of unwanted noise may be produced, even in a figure 8-shaped coil. In order to inhibit the production of unwanted noise, it is desirable for the center point of the figure 8-shaped coil and the center point of the transmitter coil L1 or the receiver coil L2 to exist on the same axis.

(2.5 Measured Data)

The results of various measurements made on a contactless power supply system 100 according the present embodiment will now be illustrated.

Figure 12:
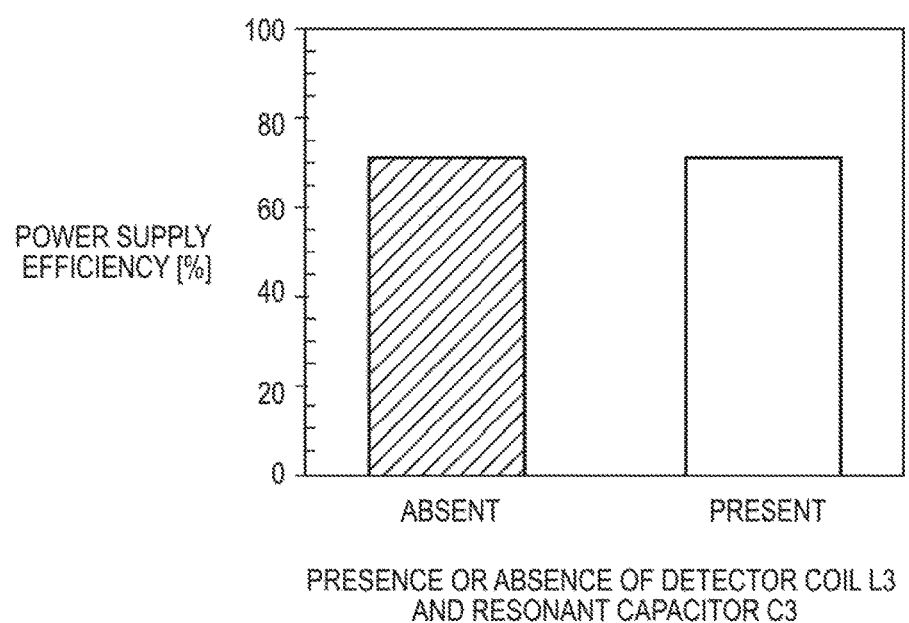
FIG. 12 is a graph illustrating an example of the difference in the power supply efficiency of a contactless power supply system according to whether or not a foreign matter detecting apparatus is present.

FIG. 12 illustrates the difference in the power supply efficiency of a contactless power supply system 100 according to whether or not a foreign matter detecting apparatus 31 is present. Herein, the detector coil L3 in the foreign matter detecting apparatus 31 is disposed inside the receiver coil L2 in a relationship like that illustrated in FIG. 6A and FIG. 6B. FIG. 12 demonstrates that there is almost no change in the power supply efficiency of a contactless power supply system 100 according to whether or not a foreign matter detecting apparatus 31 (the detector coil L3 and the resonant capacitor C3) is present. This is because, as discussed earlier, the detector coil L3 has less magnetic flux leakage from the detector coil L3, and the electrical properties (such as the Q factor and L value) of the detector coil L3 exhibit little change due to external factors (such as the metal material or magnetic material constituting the transmitter coil L1, the receiver coil L2, the magnetic shielding material 41, the power supply apparatus 10, and the electronic device 20A (20B)).

FIG. 13A and FIG. 13B illustratethe foreign metal detection accuracy of a detector coil.

FIG. 13A is a performance mapping illustrating exemplary foreign metal detection accuracy for the case of using a figure 8-shaped coil as a detector coil. Note that in FIG. 13A, the Q factor of the detector coil is assumed to be 100% in the case of packaging the detector coil inside the electronic device 20A.

If a figure 8-shaped detector coil is disposed on top of the transmitter 12 (transmitter coil L1) of the power supply apparatus 10, the detector coil is somewhat affected by the transmitter 12 (the transmitter coil L1, magnetic material, and internal metal, for example), and thus the Q factor of the detector coil drops somewhat (Q factor 47b) compared to when the power supply apparatus 10 is not present (Q factor 47a). However, since the drop in the Q factor of the detector coil is significantly greater in the case where foreign metal is disposed (Q factor 47c), foreign metal may be accurately detected.

Meanwhile, FIG. 13B is a performance mapping illustrating exemplary foreign metal detection accuracy for the case of using a spiral-shaped coil as a detector coil. Note that in FIG. 13B, the Q factor of the detector coil is assumed to be 100% in the case of packaging the detector coil inside the electronic device 20A.

If a spiral-shaped detector coil is disposed on top of the transmitter 12 (transmitter coil L1) of the power supply apparatus 10, the detector coil is greatly affected by the transmitter 12 (the transmitter coil L1, magnetic material, and internal metal, for example), and thus the Q factor of the detector coil drops significantly (Q factor 48*b*) compared to when the power supply apparatus 10 is not present (Q factor 48*a*). For this reason, the Q factor of the detector coil does not change significantly even when foreign metal is disposed (Q factors 48*b* and 48*c*), and thus the foreign metal detection accuracy worsens considerably in the case of using a spiral-shaped coil as the detector coil.

According to the first embodiment described above, applying a figure 8-shaped coil to the detector coil in a contactless power supply system equipped with a foreign matter detecting apparatus greatly improves factors such as magnetic flux leakage from the detector coil, change in the electrical properties (electrical parameters) due to external factors, and unwanted noise produced in the detector coil. Thus, it becomes possible to detect foreign metal or other foreign matter which may generate heat due to magnetic flux without providing an additional sensor, and furthermore greatly improve detection accuracy.

The present embodiment is described using an example of detecting foreign matter while contactless power supply is in operation. However, an embodiment of the present disclosure is not limited only to such cases, and various modifications are possible. For example, it is also conceivable that contactless power supply operation may be suspended or that power supplied by contactless power supply may be restricted while detecting foreign matter.

Since the unwanted noise produced in the detector coil decreases in such cases, it is not strictly necessary to make the frequency of the AC signal flowing through the detector coil differ from the frequencies of the AC signals flowing through the transmitter coil and the receiver coil. In other words, foreign matter detection may be conducted using an AC signal whose frequency is approximately equal to the frequencies (f1≈f2) of the AC signals used for contactless power supply operation. Also, in such cases particularly it is also possible to make the detector coil the same as the transmitter coil or the receiver coil.

[Modification 1]

Figure 14:
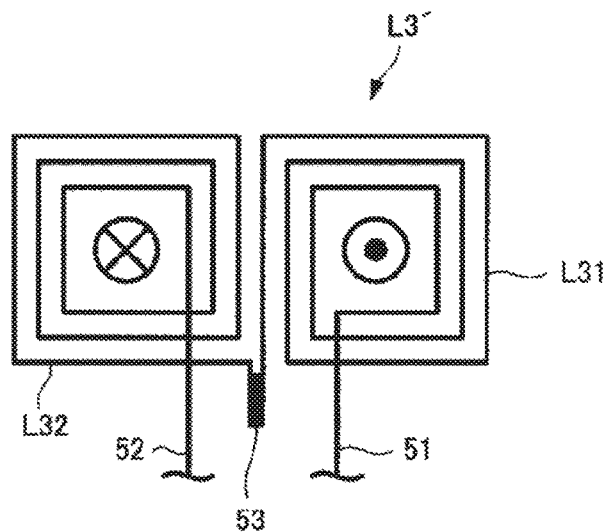
FIG. 14 is a plan view illustrating an exemplary configuration of a figure 8-shaped detector coil according to a first modification of the first embodiment of the present disclosure.

Although the foregoing first embodiment is described only for the case of using a continuous figure 8-shaped detector coil as illustrated in FIGS. 6A, 6B, 7A and 7B, a figure 8-shaped detector coil (magnetic coupling element) like that illustrated in FIG. 14 may also be used.

In the example in FIG. 14, a figure 8-shaped detector coil L3' includes spiral-shaped coils L31 and L32, with one end of the coil L31 being electrically connected (joined) in series to one end of the coil L32 using solder or a connector, for example. However, the coils L31 and L32 are connected such that the magnetic flux (magnetic field lines) produced from the coil L31 and the magnetic flux (magnetic field lines) produced from the coil L32 have approximately opposing orientations, as illustrated by FIG. 10B and the example in FIG. 14.

Note that this connection may also be an electrical parallel connection or a combined series and parallel connection.

For example, in the case of an electrical series connection, voltage may be measured using a lead 51 from the coil L31 and a lead 52 from the coil L32. In the case of an electrical parallel connection, voltage may be measured between the junction 53 of the coil L31 and the lead 51 or between the junction 53 of the coil L32 and the coil L32, taking the junction 53 between the coil L31 and the coil L32 as a reference potential point.

According to the present modification, since simple spiral-shaped coils are joined to constitute a figure 8-shaped detector coil, the electrical properties of the two coils may be easily made nearly equal compared to a continuous figure 8-shaped coil.

Although the foregoing describes an example of the case of applying a single magnetic coupling element (figure 8-shaped coil) made up of two coils to a detector coil as an example of the first embodiment of the present disclosure, the present disclosure is not limited to the foregoing embodiment, and various modifications are possible.

For example, in some cases it may be desirable to use one or multiple magnetic coupling elements shaped like multiple coils electrically connected together, in order to improve foreign matter detection accuracy, for example.

In other words, in order to further improve foreign matter detection accuracy, for example, it may be more desirable to use one or multiple magnetic coupling elements shaped like multiple coils electrically connected together, in which the magnetic flux produced from at least one or more of these multiple coils and the magnetic flux produced from the remaining of these multiple coils have approximately opposing orientations.

Hereinafter, examples of other embodiments of the present disclosure will be described with reference to the drawings. Note that structural elements like those of the first embodiment are denoted with the same reference numerals, and repeated explanation of these structural elements is omitted.

<3. Second Embodiment>

The configuration is not limited to a figure 8-shaped coil according to the first embodiment, and a square grid-shaped (in other words, a 2×2 lattice-shaped) coil may also be used as a detector coil (magnetic coupling element). Hereinafter, an example applying a square grid-shaped coil to the detector coil will be described as a second embodiment of the present disclosure.

Figure 15:
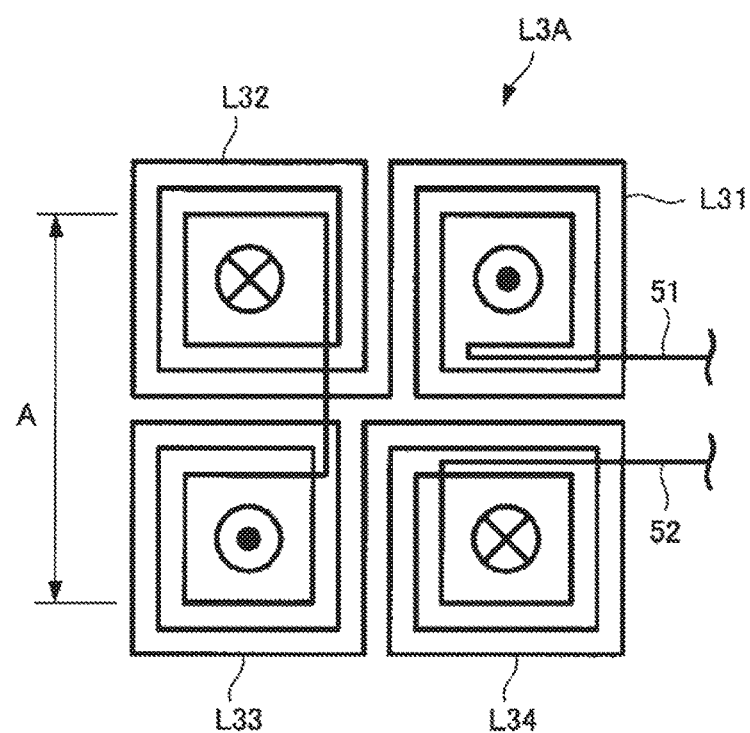
FIG. 15 is a plan view illustrating an exemplary configuration of a square grid-shaped detector coil according to the second embodiment of the present disclosure.

FIG. 15 is a plan view illustrating an exemplary configuration of a square grid-shaped detector coil according to the second embodiment of the present disclosure.

The square grid-shaped detector coil L3A includes four spiral-shaped coils L31 to L34 electrically connected (joined) in series. The coils L33 and L34 have a mostly similar configuration to the spiral-shaped coils L31 and L32. The coil L31 includes a lead 51, while the coil L34 includes a lead 52. The coil L32 and the coil L33 do not have leads, and are electrically connected to their respectively adjacent coils L31 and L34. In the detector coil L3A in this example, the coils L31 to L34 are connected such that the magnetic flux (magnetic field lines) produced from the coils L31 and L33 is of approximately opposite orientation to the magnetic flux (magnetic field lines) produced from the coils L32 and L34 at a given time (phase).

Note that this connection may also be an electrical parallel connection or a combined series and parallel connection, similarly to the example in FIG. 14.

In the present embodiment, it is likewise desirable for the relationship between the inner dimension A or the outer dimension B of the detector coil L3A and the receiver coil to be the relationship described in the first embodiment.

According to the foregoing second embodiment, action and advantages like the following are obtained in addition to the action and advantages of the first embodiment.

A detector coil according to the second embodiment is a square grid-shaped coil including four coils. Increasing the number of coils compared to the figure 8-shaped coil according to the first embodiment increases the surface area occupied by the detector coil and increases the detection range. For example, in the case of a detector coil according to the second embodiment, the detection range may be doubled compared to a detector coil of the first embodiment.

However, since a detector coil of the first embodiment has better detection accuracy, the decision to implement the first embodiment or the second embodiment may be determined according to whether detection accuracy or detection range is prioritized.

[Modification 1]

FIG. 16 is a plan view illustrating an exemplary configuration of a square grid-shaped detector coil according to a first modification of the second embodiment of the present disclosure.

The square grid-shaped detector coil L3B differs from the detector coil L3A in that the coils constituting the detector coil L3B are connected such that the magnetic flux (magnetic field lines) produced from the coils L31 and L34' on which leads 51 and 52 are formed is of approximately opposite orientation to the magnetic flux (magnetic field lines) produced from the coils L32 and L33' at a given time (phase).

Note that this connection may also be an electrical parallel connection or a combined series and parallel connection, similarly to the example in FIG. 14.

<4. Third Embodiment>

The configuration is not limited to a square grid-shaped coil according to the above second embodiment, and a lattice-shaped coil may also be used as a detector coil (magnetic coupling element). Hereinafter, an example applying a lattice-shaped coil to the detector coil will be described as a third embodiment of the present disclosure.

FIG. 17 is a plan view illustrating an exemplary configuration of a lattice-shaped detector coil according to the third embodiment of the present disclosure. The lattice-shaped detector coil L3C is configured such that multiple coils are connected in an electrical series connection, parallel connection, or a combined series and parallel connection. The example in FIG. 17 is for the case of a detector coil that includes 21 spiral-shaped coils L31 to L321 connected in series.

In the detector coil L3C, the coils L31 to L321 are disposed in a matrix parallel to the plane of the magnetic shielding material 41, for example, with the coils from the coil L31 to the coil L321 being continuously connected in sequence. For example, the coils L31 to L37 may be connected from left to right, with the coils L38 to L314 connected from right to left on the next row down, and the coils L315 to L321 connected from left to right one more row down. The coils L31 to L321 are connected such that the magnetic flux (magnetic field lines) produced from adjacent coils are of approximately opposing orientations at a given time (phase).

In this way, a detector coil may be configured such that multiple coils such as spiral-shaped coils, helical coils, or coils with a combined spiral and helical shape (in other words, coils having a basic ring shape) are connected in an electrical series connection, parallel connection, or a combined series and parallel connection. However, it is desirable for these multiple coils constituting the detector coil to be connected such that the magnetic flux (magnetic field lines) produced from at least one or more of these multiple coils and the magnetic flux (magnetic field lines) produced from the remaining of these multiple coils have approximately opposing orientations at a given time (phase).

Also, in the case where the detector coil includes multiple coils, it is particularly desirable for the total magnetic flux (magnetic field lines) produced from at least one or more coils to be approximately equal to the total magnetic flux (magnetic field lines) of approximately opposite orientation produced from the remaining coils. In this case, issues such as magnetic flux leakage from the detector coil, changes in the electrical properties (electrical parameters) of the detector coil due to external factors, and unwanted noise occurring in the detector coil decrease particularly. In order to equalize the total magnetic flux, it is desirable for there to be an even number of coils constituting the detector coil in the case where each of the multiple coils has approximately the same shape.

Furthermore, it is desirable for the number of coils producing magnetic flux (magnetic field lines) of approximately opposite orientation to be half the number of coils constituting the detector coil. In this case, since the magnetic flux distribution within the detector coil becomes approximately uniform, foreign metal detection accuracy stabilizes.

Meanwhile, it is desirable for at least one or more coils from among the multiple coils constituting the detector coil to have an inner dimension that is smaller than the inner dimension of the transmitter coil or the receiver coil.

In addition, it is desirable for the overall inner dimension of the multiple coils constituting the detector coil to be smaller than the inner dimension of the transmitter coil or the receiver coil. The overall inner dimension of the multiple coils constituting the detector coil may be either the inner dimension A along the shorter edge or the inner dimension A' along the longer edge, as illustrated in FIG. 17.

Furthermore, it is particularly desirable for the overall outer dimension of the detector coil to be smaller than the inner dimension of the transmitter coil or the receiver coil.

These parameters are for decreasing change in the electrical properties (such as the Q factor and L value) of the detector coil due to external factors. Also, in order to effectively suppress unwanted noise produced in the detector coil, it is desirable for the shape of the detector coil to be an approximately symmetrical shape, such as by having approximate rotational symmetry, approximate line symmetry, or approximate point symmetry. However, the configuration is not limited thereto in the case where it is desirable to extend the foreign metal detection range even if the foreign metal detection accuracy drops.

According to the third embodiment discussed above, the number of coils constituting the detector coil is further increased compared to the second embodiment, and thus the detection range of the detector coil is significantly extended.

<5. Fourth Embodiment>

Although the foregoing first through third embodiments are described for the case of providing one detector coil, an embodiment of the present disclosure is not limited to such a case, and may also be configured such that two or more detector coils (magnetic coupling elements) are multiply provided, as illustrated in FIGS. 18 and 19, for example. Correspondingly, the foreign matter detecting apparatus 31 may also be multiply provided. Alternatively, it may be configured such that one or multiple foreign matter detecting apparatus are able to switch among multiply disposed detector coils.

FIG. 18 is a plan view of a detector coil unit 61 in which two figure 8-shaped detector coils are disposed according to the fourth embodiment of the present disclosure.

In the detector coil unit 61 in this example, two detector coils L3-1 and L3-2 are disposed adjacent to each other on the sides which are opposite the sides having their respective leads 51 and 52. The detector coils L3-1 and L3-2 each have a configuration similar to the detector coil L3', with a single detector coil including two spiral-shaped coils. However, the detector coil unit 61 in this example obviously may also be configured using the detector coil L3.

Herein, the respective conductive lines of the detector coil L3-1 and the detector coil L3-2 may also be disposed overlapping by a given amount. By disposing the detector coil L3-1 and the detector coil L3-2 in this way, their detection ranges overlap, which resolves the problem of a dead zone between the detector coil L3-1 and the detector coil L3-2 where foreign matter is not detected.

[Modification 1]

FIG. 19 is a plan view illustrating a detector coil unit in which two figure 8-shaped detector coils are disposed according to a first modification of the fourth embodiment of the present disclosure.

In the detector coil unit 62 in this example, two detector coils L3-1 and L3-2' are disposed adjacent to each other on the sides which are opposite the sides having their respective leads 51 and 52. The coil L31' and the coil L32' of the detector coil L3-2' have a magnetic flux (magnetic field lines) orientation that is the reverse of the coil L31 and the coil L32 of the detector coil L3-2.

Meanwhile, in the multiple detector coils illustrated in FIGS. 18 and 19, it is desirable for at least one or more coils from among the multiple coils constituting each detector coil to have an inner dimension that is smaller than the inner dimension of the transmitter coil or the receiver coil.

In addition, it is desirable for the overall inner dimension of the multiple coils constituting the multiple detector coils to be smaller than the inner dimension of the transmitter coil or the receiver coil.

Furthermore, it is particularly desirable for the overall outer dimension of the multiple detector coils to be smaller than the inner dimension of the transmitter coil or the receiver coil.

The above is for decreasing change in the electrical properties (such as the Q factor and L value) of the detector coil due to external factors.

Also, in order to effectively suppress unwanted noise produced in the multiple detector coils, it is desirable for the multiple detector coils to be disposed so as to form an approximately symmetrical shape, such as by having approximate rotational symmetry, approximate line symmetry, or approximate point symmetry. However, the configuration is not limited thereto in the case where it is desirable to extend the foreign metal detection range even if the foreign metal detection accuracy drops.

According to the fourth embodiment discussed above, a single foreign matter detecting apparatus is provided with respect to a detector coil unit having multiple detector coils (magnetic coupling elements), such that multiple detector coils may be used by switching among them in a time division. Also, multiple foreign matter detecting apparatus may be provided such that one of the multiple detector coils may be used as a main detector coil while using the remaining detector coils as auxiliary detector coils.

Note that in the case where the outer dimension across one or multiple detector coils made up of multiple coils is greater than the inner dimension of the receiver coil (or the transmitter coil), it may be difficult to dispose part or all of the one or multiple detector coils in the same plane as the receiver coil (or the transmitter coil). In such cases, it is anticipated that a magnetic or other material may be disposed between all or at least part of the one or multiple detector coils and the receiver coil (or the transmitter coil). This is in order to mitigate drops in the Q factor of the one or multiple detector coils in the case where the one or multiple detector coils are disposed on top of the winding part or the pattern part of the receiver coil (or the transmitter coil).

<6. Fifth Embodiment>

Next, an example in which a receiver coil and multiple detector coils (magnetic coupling elements) are disposed outside the same plane will be described as a fifth embodiment of the present disclosure.

Figure 20A:
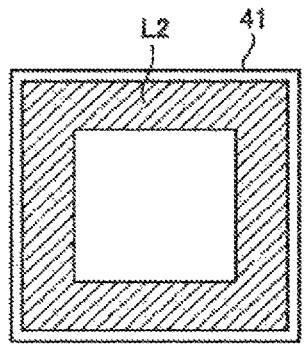
FIGS. 20A to 20C are explanatory diagrams for exemplary detector coil arrangements according to the fifth embodiment of the present disclosure, where
Figure 20B:
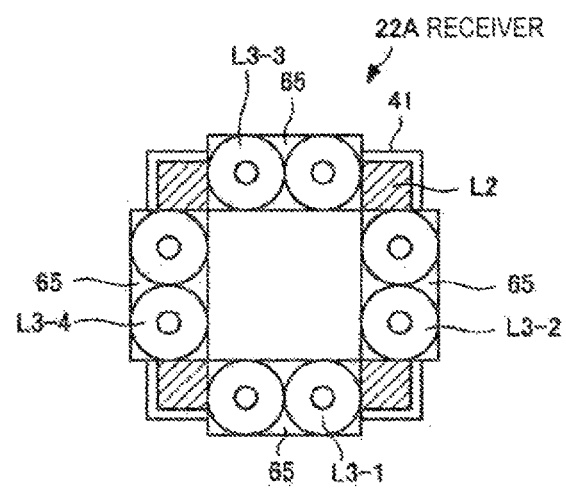
Figure 20C:
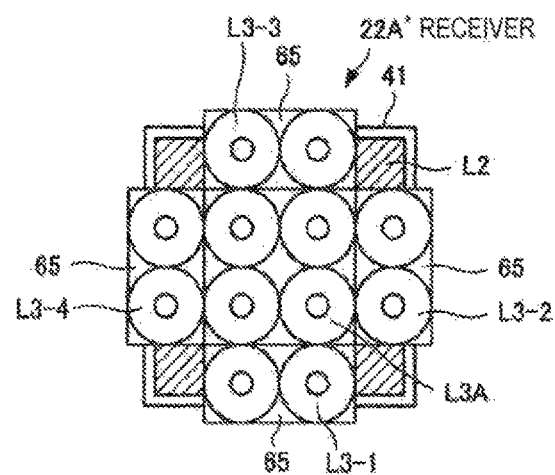

FIGS. 20A to 20C are explanatory diagrams for an exemplary detector coil arrangement according to the fifth embodiment of the present disclosure. FIGS. 20A, 20B, and 20C are plan views illustrating an example of a receiver coil, an example in which multiple detector coils are disposed on top of the receiver coil, and an example in which some detector coils are disposed in the center of the receiver coil, respectively.

In the receiver 22A illustrated in FIG. 20A, a receiver coil L2 is disposed on top of magnetic shielding material 41 (FIG. 20A), with detector coils L3-1 to L3-4, for example, disposed on top of the receiver coil L2 via magnetic material 65.

The receiver coil L2 is formed by multiply winding conductive wire in a spiral shape (such as an approximately circular shape, an approximately elliptical shape, or an approximately rectangular shape) in the same plane. In this example, conductive wire is wound in an approximately square spiral. Along each of the four edges of the approximately square receiver coil L2, there is placed magnetic material 65 of approximately the same size as the horizontal and vertical Feret diameters (projection widths) of the detector coils L3-1 to L3-4. Additionally, the detector coils L3-1 to L3-4 are disposed on top of the respective magnetic material 65.

The detector coils L3-1 to L3-4 may be four continuously connected figure 8-shaped coils, or split into multiple detector coils, as illustrated in FIGS. 15 to 19.

Experiment has confirmed that foreign metal may be detected with the foregoing fifth embodiment, similarly to the second through fourth embodiments, even in the case where the receiver coil and the detector coil are disposed outside the same plane, or in other words, even when not disposed on the same plane in the Z direction.

Note that although it is desirable to dispose magnetic material between the receiver coil L2 and the detector coils L3-1 to L3-4 as illustrated in FIG. 20B in order to mitigate drops in the Q factor of the detector coils, the configuration is not limited thereto.

In addition, a receiver 22A' may also be configured by disposing detector coils in the center of the receiver coil L2, as illustrated in FIG. 20C. In this case, it is also conceivable to dispose some of the detector coils (such as the detector coils L3A in FIG. 20C, for example) in the same plane as the receiver coil L2, while disposing the remaining detector coils outside the same plane as the receiver coil L2. Obviously, all detector coils may also be disposed outside the same plane as the receiver coil L2.

<7. Sixth Embodiment>

Next, exemplary countermeasures for the case where foreign metal generates heat over a wide range will be described as the sixth embodiment of the present disclosure.

Figure 21A:
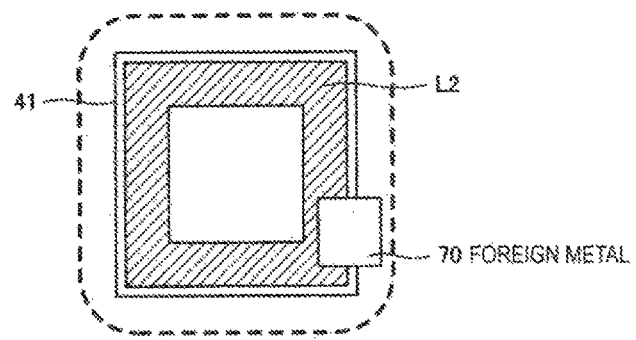
FIGS. 21A to 21C are explanatory diagrams for exemplary detector coil arrangements according to the sixth embodiment of the present disclosure, where
Figure 21B:
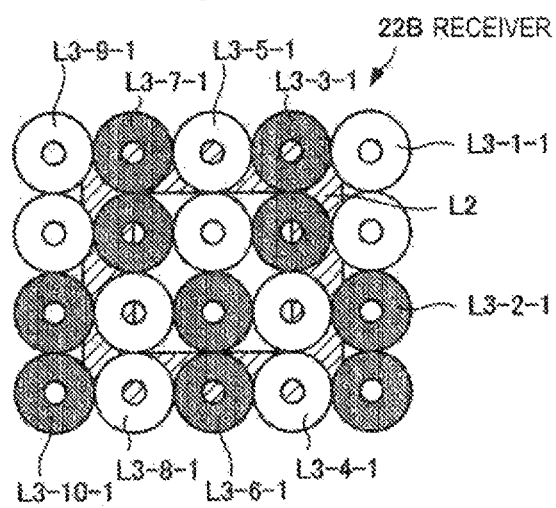
Figure 21C:
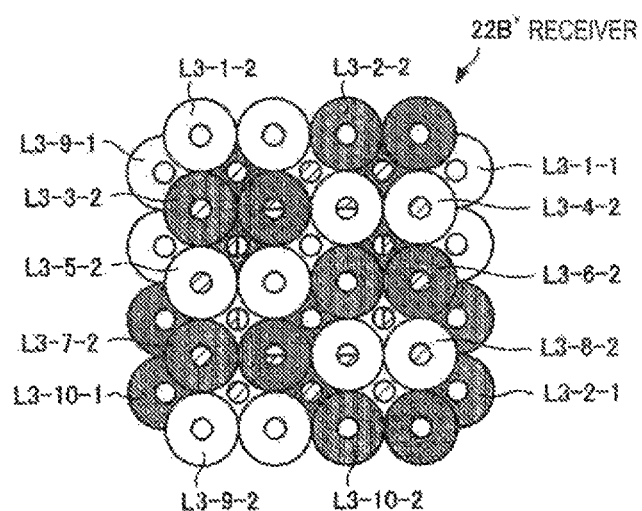

FIG. 21A and FIG. 21B are explanatory diagrams for an exemplary detector coil (magnetic coupling element) arrangement according to the sixth embodiment of the present disclosure. FIGS. 21A, 21B, and 21C are plan views illustrating an example of a receiver coil and foreign metal, an example in which multiple detector coils are disposed on top of the receiver coil, and an example in which multiple detector coils are additionally disposed on top of the multiple detector coils in FIG. 21B, respectively.

As illustrated in FIG. 21A, it is conceivable that foreign metal 70 may generate heat over a wide area on the outside of the receiver coil L2 (the area enclosed by broken lines). In cases where foreign metal generates heat over a wide area in this way, it is conceivable to dispose multiple detector coils over a wide area as a countermeasure.

In the receiver 22B illustrated in FIG. 21B, 10 figure 8-shaped detector coils L3-1-1 to L3-10-1, for example, are disposed on top of the receiver coil L2. The overall horizontal and vertical Feret diameters of these 10 detector coils are greater than the receiver coil L2. In FIG. 21B, the detector coils are alternately shaded and unshaded in order to distinguish between adjacent figure 8-shaped detector coils.

However, in the case of the exemplary arrangement in FIG. 21B, a dead zone where foreign metal is not detected may exist between a given detector coil and an adjacent detector coil. For this reason, in some cases it may also be desirable to dispose detector coils in two or more layers, like in the exemplary arrangement in FIG. 21C. Herein, a receiver 22B' is configured by disposing 10 detector coils L3-1-1 to L3-10-1 (the first layer) on top of the receiver coil L2, and additionally disposing 10 more detector coils L3-1-2 to L3-10-2 (the second layer) on top of the first layer.

At this point, the problem of a dead zone between adjacent detector coils may be resolved by disposing the second layer of detector coils shifted by ½ pitch with respect to the first layer of detector coils. Also, if the figure 8-shaped detector coils in the first layer are arranged vertically (in the Y direction) and the detector coils in the second layer are arranged horizontally (in the X direction), it is possible to detect magnetic flux changes in a different direction than the first layer of detector coils, thus reliably resolving the dead zone problem and improving foreign metal detection accuracy.

According to the foregoing sixth embodiment, it is possible to detect foreign metal over a wide range of the receiver coil. Also, by disposing the detector coils in two or more layers, it becomes possible to resolve the problem of dead zones where foreign metal is not detected.

[Modification 1]

Figure 22A:
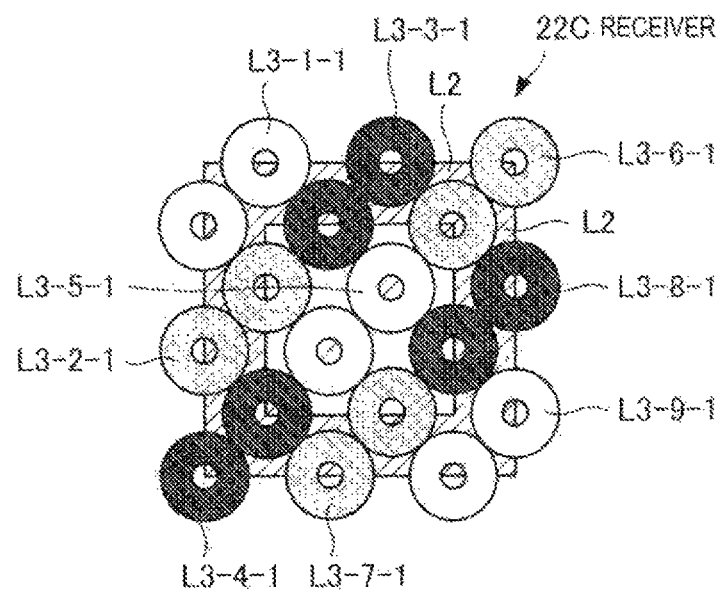
FIG. 22A and FIG. 22B are explanatory diagrams for exemplary detector coil arrangements according to a first modification of the sixth embodiment of the present disclosure, where
Figure 22B:
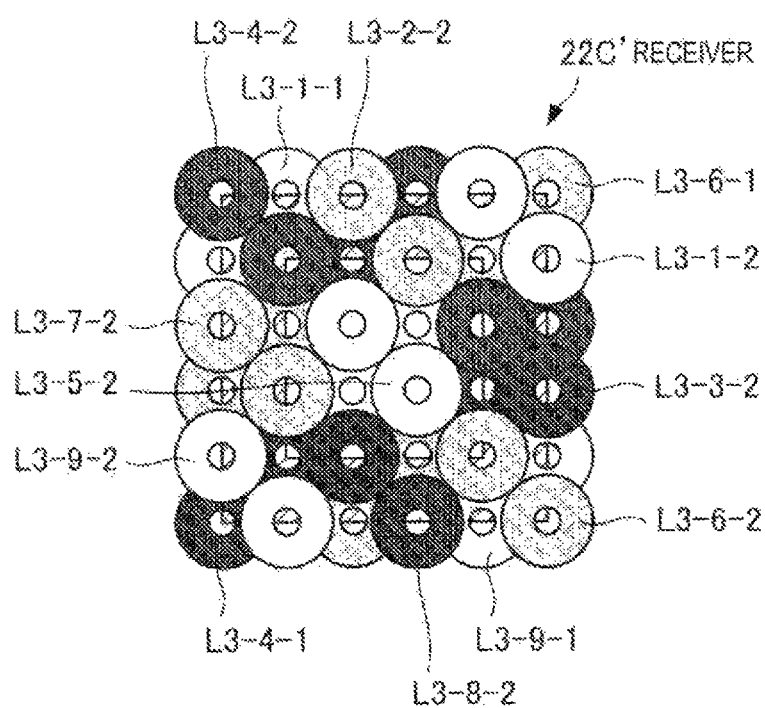

FIG. 22A and FIG. 22B are explanatory diagrams for exemplary detector coil arrangements according to a first modification of the sixth embodiment of the present disclosure. FIGS. 22A and 22B are plan views illustrating an example in which multiple detector coils are disposed on top of the receiver coil, and an example in which multiple detector coils are additionally disposed on top of the multiple detector coils in FIG. 22A, respectively.

Whereas detector coils are disposed in the horizontal and vertical directions of the receiver 22B according to the sixth embodiment illustrated in FIG. 21A and FIG. 21B, detector coils are disposed in the diagonal direction of the receiver coil in the example illustrated in FIG. 22A and FIG. 22B.

In the receiver 22C illustrated in FIG. 22B, nine figure 8-shaped detector coils L3-1-1 to L3-9-1, for example, are disposed on top of the receiver coil L2 in the diagonal direction of the approximately square receiver coil L2. The overall horizontal and vertical Feret diameters of these nine detector coils are greater than the receiver coil L2. In FIG. 22B, the detector coils are alternately unshaded, shaded gray, and shaded black in order to distinguish between adjacent figure 8-shaped detector coils.

Also, in order to resolve the problem of a dead zone between adjacent detector coils, a receiver 22C' is configured by disposing a first layer of detector coils L3-1-1 to L3-9-1 on top of the receiver coil L2, and disposing a second layer of detector coils L3-1-2 to L3-9-2 on top of the first layer. At this point, the second layer of detector coils L3-1-2 to L3-9-2 are disposed in a different diagonal direction than that of the first layer of detector coils L3-1-1 to L3-9-1.

According to this example, a second layer of detector coils is disposed in a different diagonal direction that that of the first layer of detector coils, thereby making it possible to detect magnetic flux changes in a different direction than the first layer of detector coils, and thus reliably resolving the dead zone problem and improving foreign metal detection accuracy.

<8. Other>

The foregoing first through sixth embodiments are described for the case of providing a foreign matter detecting apparatus including one or more detector coils in an electronic device given as a secondary device (power recipient device).

However, an embodiment of the present disclosure is not limited to such a case, and may also be configured such that a foreign matter detecting apparatus including one or more detector coils is provided in a power supply apparatus given as a primary device. In such cases, the receiver coil described in the foregoing first embodiment may be substituted with a transmitter coil, and the transmitter coil may be substituted with a receiver coil. A foreign matter detecting apparatus including one or more detector coils may also be disposed in both a primary device and a secondary device.

Furthermore, it may also be configured such that a foreign matter detecting apparatus including one or more detector coils is provided in another apparatus separate from a primary device and a secondary device.

In other words, it may be configured such that the foreign matter detecting apparatus including one or more detector coils described in the foregoing embodiments is provided in at least one of a primary device, a secondary device given as a power recipient device, or another apparatus separate from the primary device and the secondary device.

Also, in the description of the foregoing embodiments, there is described the example of a system (such as a foreign matter detecting apparatus, for example) that detects the presence of foreign matter from change in the Q factor of a magnetic coupling element (detector coil), or from change in the Q factor of an LC resonator (resonant circuit) that at least includes a magnetic coupling element. However, the above system is not limited to such an example, and may also be a foreign matter detection system that detects the presence of foreign matter using a separate technique related to a magnetic coupling element.

For example, a case is also conceivable in which foreign matter is detected on the basis of other electrical parameters which are calculated (estimated, indirectly measured) on the basis of measurement results for the Q factor of a magnetic coupling element, or measurement results for the Q factor of an LC resonator (resonant circuit) that at least includes a magnetic coupling element.

Also conceivable is a case in which foreign matter is detected on the basis of changes in some kind of electrical property (electrical parameter) related to an individual magnetic coupling element, or to an apparatus and system that utilize a magnetic coupling element. Potential examples of such an electrical property (electrical parameter) include a power value, a voltage value, a current value, a power factor, an energy efficiency, a power supply efficiency, a charging efficiency, an energy loss, the amplitude, phase, period, pulse width, or duty cycle of a detection signal, an impedance value, a mutual inductance value, a coupling coefficient, a magnetic flux magnitude, a magnetic flux density, a capacitance value, a self-inductance value, a resonant frequency, a carrier wave frequency, a signal wave frequency, a modulation factor, a signal level, a noise level, and a temperature, for example.

Additionally, it is also conceivable that in a foreign matter detection system according to an embodiment of the present disclosure, multiple foreign matter detection techniques rather than just one of the foreign matter detection techniques discussed above may be combined and utilized jointly.

Although the foregoing embodiments are described only for the case of providing one transmitter coil and receiver coil each, an embodiment of the present disclosure is not limited to such a case, and may also be configured such that multiple (two or more) transmitter coils or receiver coils are provided, for example.

In addition, other LC resonators (resonant circuits) besides the LC resonator (resonant circuit) discussed earlier may be used in a contactless power supply system (for contactless power supply functionality or foreign matter detection functionality).

Also, although in the foregoing embodiments each coil (transmitter coil, receiver coil, detector coil) is taken to be spiral-shaped (planar) or helically wound in the direction of thickness, an embodiment of the present disclosure is not limited to such examples. For example, each coil may also have an alpha-winding shape in which a spiral-shaped coil folds back on itself in two layers, or spiral shapes with additional layers, for example.

The transmitter coil and receiver coil may also be configured with a coil whose shape enables reduced magnetic flux leakage, such as a figure 8 shape, a square grid shape, or a lattice shape.

The detector coil may also be integrated with a transmitter coil or a receiver coil, and a contactless power supply coil such as a transmitter coil or a receiver coil may be jointly used as a detector coil. Moreover, a coil used for purposes other than contactless power supply, such as an induction heating coil or a wireless communication coil may also be jointly used as a detector coil.

In other words, although the foregoing embodiments are described using the example of the case where a magnetic coupling element is taken to be a detector coil, it is also conceivable for the magnetic coupling element to be a coil such as a coil for contactless power supply (a transmitter coil or a receiver coil), an induction heating coil, or a wireless communication coil, such that these coils are also used for the purpose of detecting foreign matter.

Also, material such as magnetic material or metal material may also be provided in the transmitter of the power transmitting apparatus, in the receiver of the power receiving apparatus, and in the vicinity of the one or more detector coils, for the purpose of mitigating unwanted magnetic flux (magnetic field lines; magnetic field) leakage and improving transfer efficiency (power supply efficiency), for example.

Also, the respective resonant capacitors (particularly the resonant capacitor in the foreign matter detecting apparatus) are not limited to the case of using fixed capacitance values, and may also be configured with variable electrostatic capacitance values (such as a configuration that uses switches or other components to switch among connection pathways for multiple capacitive elements, for example). Configuring the resonant capacitors in this way makes it possible to control (optimize) the resonant frequency by adjusting the electrostatic capacitance values.

In addition, although the foregoing embodiments are described with reference to specific components of a power supply apparatus and an electronic device, for example, it is not necessary to provide all of the components, and furthermore, other components may be additionally provided. For example, it may also be configured such that a power supply apparatus (power transmitting apparatus) or an electronic apparatus (power receiving apparatus) is provided with communication functionality, some kind of detection functionality, control functionality, display functionality, functionality for authenticating a secondary device, functionality for determining that a secondary device is on top of a primary device, and functionality for detecting the presence of foreign matter according to a different technique than that according to an embodiment of the present disclosure, for example.

Also, although the foregoing embodiments are described by taking an example for the case of using load modulation for communication functionality, an embodiment of the present disclosure is not limited to such a case. For example, a modulation technique other than load modulation may also be used for communication functionality, or components such as a wireless communication antenna or wireless communication coil may be provided to communicate according to a technique other than modulation. Meanwhile, depending on the configuration of the contactless power supply functionality (the power transmitting apparatus and the power receiving apparatus) and the foreign matter detection functionality (the foreign matter detecting apparatus), it may also be configured such that communication functionality itself is not provided. Similarly, depending on the configuration of the contactless power supply functionality (the power transmitting apparatus and the power receiving apparatus) and the foreign matter detection functionality (the foreign matter detecting apparatus), it may also be configured such that portions of the various components (such as parts, units, and circuits) used in the description of the foregoing embodiments are not provided.

Also, although the foregoing embodiments are described by taking a example for the case where multiple (two) electronic devices are provided in a contactless power supply system, an embodiment of the present disclosure is not limited to such an example, and one electronic device, or three or more electronic devices, may also be provided in the contactless power supply system.

Furthermore, although the foregoing embodiments are described by taking a charging tray for portable electronic devices (CE devices) such as mobile phones as an example of a power supply apparatus, the power supply apparatus is not limited to such consumer charging trays, and is applicable as a charging device for various types of electronic devices. Moreover, it is not strictly necessary for the power supply apparatus to be a tray, and may also be a stand for an electronic device, such as a cradle, for example.

Also, although the foregoing embodiments are described by taking an electronic device as an example of a power recipient device, the power recipient device is not limited thereto, and may also be a power recipient device other than an electronic device (such as an electric car or other vehicle, for example).

Additionally, the present technology may also be configured as below.

(1) A detecting apparatus including:
one or a plurality of magnetic coupling elements that include a plurality of coils; and
a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present, wherein, in the one or plurality of magnetic coupling elements, the plurality of coils are electrically connected such that magnetic flux produced from at least one or more of the plurality of coils and magnetic flux produced from remaining coils of the plurality of coils have approximately opposing orientations.

(2) The detecting apparatus according to (1), wherein the electrical parameter is a Q factor of the one or plurality of magnetic coupling elements or of a circuit that at least includes the one or plurality of magnetic coupling elements.

(3) The detecting apparatus according to (1) or (2), wherein
a dimension of an innermost perimeter of at least one or more coils from among the plurality of coils included in the one or plurality of magnetic coupling elements is smaller than a dimension of an innermost perimeter of a contactless power supply coil used for contactless power supply.

(4) The detecting apparatus according to (3), wherein
a dimension of an outermost perimeter of at least one or more coils from among the plurality of coils included in the one or plurality of magnetic coupling elements is smaller than the dimension of the innermost perimeter of the contactless power supply coil.

(5) The detecting apparatus according to any one of (1) to (4), wherein
a center point of the one or plurality of magnetic coupling elements and a center point of the contactless power supply coil are positioned on approximately a same axis.

(6) The detecting apparatus according to any one of (3) to (5), wherein
a total area of regions inside innermost perimeters of the plurality of coils included in the one or plurality of magnetic coupling elements is smaller than an area of a region inside the innermost perimeter of the contactless power supply coil.

(7) The detecting apparatus according to any one of (4) to (6), wherein
a total area of regions inside outermost perimeters of the plurality of coils included in the one or plurality of magnetic coupling elements is smaller than an area of a region inside the innermost perimeter of the contactless power supply coil.

(8) The detecting apparatus according to any one of (1) to (7), wherein
a total magnetic flux of approximately a same orientation and a total magnetic flux of approximately an opposite orientation that are produced from the plurality of coils included in the one or plurality of magnetic coupling elements are approximately identical.

(9) The detecting apparatus according to any one of (1) to (8), wherein
a number of the plurality of coils included in the one or plurality of magnetic coupling elements is even.

(10) The detecting apparatus according to any one of (1) to (9), wherein
the plurality of coils included in at least one magnetic coupling element from among the one or plurality of magnetic coupling elements are disposed in a FIG. 8 shape, a square grid shape, or a lattice shape.

(11) The detecting apparatus according to any one of (1) to (10), wherein
the plurality of coils included in the one or plurality of magnetic coupling elements are electrically connected in a series connection, a parallel connection, or a combined series and parallel connection.

(12) The detecting apparatus according to any one of (1) to (11), wherein
the one or plurality of magnetic coupling elements are disposed in a symmetrical shape having any of rotational symmetry, line symmetry, or point symmetry.

(13) The detecting apparatus according to any one of (1) to (12), wherein
the one or plurality of magnetic coupling elements and a contactless power supply coil used for contactless power supply are disposed on approximately a same plane.

(14) The detecting apparatus according to any one of (1) to (13), wherein
a contactless power supply coil used for contactless power supply is a transmitter coil provided in a power source device, or a receiver coil provided in a power recipient device.

(15) The detecting apparatus according to any one of (1) to (14), wherein
the circuit that at least includes the one or plurality of magnetic coupling elements is a resonant circuit.

(16) A power receiving apparatus including:
a receiver coil used for contactless power supply from a power source;
one or a plurality of magnetic coupling elements that include a plurality of coils; and
a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present,
wherein, in the one or plurality of magnetic coupling elements, the plurality of coils are electrically connected such that magnetic flux produced from at least one or more of the plurality of coils and magnetic flux produced from remaining coils of the plurality of coils have approximately opposing orientations.

(17) A power transmitting apparatus including:
a transmitter coil used for contactless power supply for a power recipient;
one or a plurality of magnetic coupling elements that include a plurality of coils; and
a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present,
wherein, in the one or plurality of magnetic coupling elements, the plurality of coils are electrically connected such that magnetic flux produced from at least one or more of the plurality of coils and magnetic flux produced from remaining coils of the plurality of coils have approximately opposing orientations.

(18) A contactless power supply system including:
a power transmitting apparatus that wirelessly transmits power; and
a power receiving apparatus that receives power from the power transmitting apparatus,
wherein at least one of the power transmitting apparatus or the power receiving apparatus includes
one or a plurality of magnetic coupling elements that include a plurality of coils, and
a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present, and wherein, in the one or plurality of magnetic coupling elements, the plurality of coils are electrically connected such that magnetic flux produced from at least one or more of the plurality of coils and magnetic flux produced from remaining coils of the plurality of coils have approximately opposing orientations.

Note that the series of operations in the foregoing embodiments may be executed in hardware, and may also be executed in software. In the case of executing the series of operations in software, a program constituting such software may be executed by a computer built into special-purpose hardware, or alternatively, by a computer onto which programs for executing various functions are installed. For example, a program constituting the desired software may be installed and executed on a general-purpose personal computer.

Also, a recording medium storing program code of software that realizes the functionality of the foregoing embodiments may also be supplied to a system or apparatus. It is furthermore obvious that the functionality is realized by a computer (or CPU or other control apparatus) in such a system or apparatus retrieving and executing the program code stored in the recording medium.

The recording medium used to supply program code in this case may be a flexible disk, hard disk, optical disc, magneto-optical disc, CD-ROM, CD-R, magnetic tape, non-volatile memory card, or ROM, for example.

Also, the functionality of the foregoing embodiments may realized by a computer executing retrieved program code. In addition, some or all of the actual operations may be conducted on the basis of instructions from such program code by an OS or other software running on the computer. This also encompasses cases where the functionality of the foregoing embodiments is realized by such operations.

Also, in this specification, the processing steps stating operations in a time series obviously encompass operations conducted in a time series following the described order, but also encompass operations executed in parallel or individually (by parallel processing or object-orientated processing, for example), without strictly being processed in a time series.

It should be understood by those skilled in the art that various modifications, combinations, sub-combinations and alterations may occur depending on design requirements and other factors insofar as they are within the scope of the appended claims or the equivalents thereof.

In other words, since the foregoing exemplary embodiments are ideal, specific examples of the present disclosure, various technically preferable limitations have been imposed thereon. However, the technical scope of the present disclosure it not to be limited to these embodiments, unless statements that particularly limit the present disclosure are made in their respective descriptions. For example, factors such as the types and quantities of materials used, processing times, processing sequences, and numerical conditions for respective parameters cited in the foregoing description are merely idealized examples. Furthermore, the dimensions, shapes, and positional relationships illustrated in the drawings used in the description are general and diagrammatic.

What is claimed is:

1. A power transmitting apparatus, comprising:
a first coil in a first layer;
a second coil, in a second layer, that overlaps the first coil; and
a third coil, in a third layer, that overlaps the first coil and the second coil,
wherein the third coil comprises a first sub coil, a second sub coil, a third sub coil, and a fourth sub coil that are connected in series, the first sub coil and the third sub coil produce a first magnetic flux in a first orientation, and the second sub coil and the fourth sub coil produce a second magnetic flux in a second orientation, wherein the first orientation is different from the second orientation, and
wherein an outer end of the first sub coil is connected to an outer end of the second sub coil, and an inner end of the second sub coil is connected to an inner end of the third sub coil.

2. The power transmitting apparatus according to claim 1, wherein the first coil is configured to wirelessly supply power to a power receiving apparatus.

3. The power transmitting apparatus according to claim 2, wherein the power transmitting apparatus and the power receiving apparatus are linked based on electromagnetic induction.

4. The power transmitting apparatus according to claim 2, wherein at least one of the first coil, the second coil, or the third coil has at least one of a rotational symmetry, a line symmetry, or a point symmetry.

5. The power transmitting apparatus according to claim 1, wherein the second coil is configured to wirelessly supply power to a power receiving apparatus.

6. The power transmitting apparatus according to claim 1, wherein the third coil is configured to wirelessly supply power to a power receiving apparatus.

7. The power transmitting apparatus according to claim 1, wherein at least one of the first coil or the second coil is configured to transmit power to a power receiving apparatus.

8. The power transmitting apparatus according to claim 1, wherein at least one of the first coil, the second coil, or the third coil is configured to detect a foreign matter between the power transmitting apparatus and a power recipient.

9. The power transmitting apparatus according to claim 8, wherein the power transmitting apparatus is configured to detect a change in Q factor of at least one of the first coil, the second coil, the third coil, or a circuit that includes at least one of the first coil, the second coil, or the third coil.

10. The power transmitting apparatus according to claim 9, wherein the circuit is a resonant circuit.

11. The power transmitting apparatus according to claim 1, wherein the first coil, the second coil, and the third coil are configured to generate the first magnetic flux of the first orientation and the second magnetic flux of the second orientation that is opposite to the first orientation, wherein the first magnetic flux is equal to the second magnetic flux.

12. The power transmitting apparatus according to claim 1, wherein at least one of the second coil or the third coil is in one of a shape of numeral eight, a square grid shape, or a lattice shape.

13. The power transmitting apparatus according to claim 12, wherein a magnetic shielding material is between a housing of the power transmitting apparatus and the second coil.

14. The power transmitting apparatus according to claim 1, wherein the first coil is configured to transmit power to a power recipient, and at least one of the second coil or the third coil is configured to detect a foreign matter between the power transmitting apparatus and the power recipient.

15. The power transmitting apparatus according to claim 1, wherein a first dimension of an innermost perimeter of the second coil is greater than a second dimension of an innermost perimeter of the third coil.

16. A contactless power supply system, comprising:
a power transmitting apparatus configured to wirelessly transmit power; and
a power receiving apparatus configured to receive the power from the power transmitting apparatus,
wherein at least one of the power transmitting apparatus or the power receiving apparatus includes:
a first coil in a first layer;
a second coil, in a second layer, that overlaps the first coil; and
a third coil, in a third layer, that overlaps the first coil and the second coil,
wherein the third coil comprises a first sub coil, a second sub coil, a third sub coil, and a fourth sub coil that are connected in series, the first sub coil and the third sub coil produce a first magnetic flux in a first orientation, and the second sub coil and the fourth sub coil produce a second magnetic flux in a second orientation, wherein the first orientation is different from the second orientation, and
wherein an outer end of the first sub coil is connected to an outer end of the second sub coil, and an inner end of the second sub coil is connected to an inner end of the third sub coil.

* * * * *